US010835144B2

(12) United States Patent
Wei

(10) Patent No.: US 10,835,144 B2
(45) Date of Patent: Nov. 17, 2020

(54) ELECTROENCEPHALOGRAPH, BRAIN WAVE MEASUREMENT METHOD, BRAIN WAVE MEASUREMENT SYSTEM

(71) Applicant: EKG Technology Lab, Inc., Funabashi-Shi (JP)

(72) Inventor: Daming Wei, Funabashi (JP)

(73) Assignee: EKG Technology Lab, Inc., Funabashi-Shi (JP)

( * ) Notice: Subject to any disclaimer, the term of this patent is extended or adjusted under 35 U.S.C. 154(b) by 736 days.

(21) Appl. No.: 15/520,490

(22) PCT Filed: Oct. 22, 2014

(86) PCT No.: PCT/JP2014/078058
§ 371 (c)(1),
(2) Date: Apr. 20, 2017

(87) PCT Pub. No.: WO2016/063370
PCT Pub. Date: Apr. 28, 2016

(65) Prior Publication Data
US 2017/0311837 A1 Nov. 2, 2017

(51) Int. Cl.
*A61B 5/00* (2006.01)
*A61B 5/0478* (2006.01)
(Continued)

(52) U.S. Cl.
CPC .......... *A61B 5/0478* (2013.01); *A61B 5/0476* (2013.01); *A61B 5/04845* (2013.01);
(Continued)

(58) Field of Classification Search
CPC ............... A61B 5/0476; A61B 5/6803; G06T 2207/30016; A61N 1/0456;
(Continued)

(56) References Cited

U.S. PATENT DOCUMENTS 4,716,907 A * 1/1988 Nakamura ........... A61B 5/0484
600/544
5,999,846 A * 12/1999 Pardey ................. A61B 5/0476
600/544
(Continued)

FOREIGN PATENT DOCUMENTS

CN 102711601 A 10/2012
CN 102727193 A 10/2012
(Continued)

OTHER PUBLICATIONS

International Preliminary Report on Patentability with English Translation for International Application No. PCT/JP2014/078058, dated May 4, 2017.
(Continued)

*Primary Examiner* — May A Abouelela
(74) *Attorney, Agent, or Firm* — Faegre Drinker Biddle & Reath LLP

(57) ABSTRACT

The object is to acquire electroencephalogram of high resolution with fewer number of electrodes than usual. An electroencephalogram measurement apparatus comprising: a plurality of electrodes 110 attached on the scalp of a subject for acquisition of electroencephalogram signals of the subject; and an electroencephalogram generation unit 150 for generating an electroencephalograms at locations of the scalp where the electrodes are attached and electroencephalograms at locations of the scalp where the electrodes are not attached.

9 Claims, 21 Drawing Sheets

(51) Int. Cl.
*A61B 5/0476* (2006.01)
*A61B 5/0484* (2006.01)
*A61B 5/048* (2006.01)

(52) U.S. Cl.
CPC ............ *A61B 5/7203* (2013.01); *A61B 5/048* (2013.01); *A61B 5/726* (2013.01)

(58) Field of Classification Search
CPC ...... A61N 1/36025; A61N 2/006; A61N 1/40; A61N 1/0484; A61N 1/36007; A61N 1/0529; A61N 1/36064
USPC .................. 600/300, 301, 544, 545; 434/236
See application file for complete search history.

(56) References Cited

U.S. PATENT DOCUMENTS

| | | | |
|---|---|---|---|
| 8,843,193 B2 | 9/2014 | Wei et al. | |
| 8,914,100 B2 | 12/2014 | Adachi et al. | |
| 2004/0054297 A1* | 3/2004 | Wingeier | A61B 5/0031 600/544 |
| 2006/0135879 A1* | 6/2006 | Liley | A61B 5/4821 600/544 |
| 2009/0326404 A1* | 12/2009 | Sajda | A61B 5/048 600/544 |
| 2010/0204604 A1* | 8/2010 | Liley | A61B 5/048 600/544 |
| 2011/0040202 A1* | 2/2011 | Luo | A61B 5/04842 600/544 |
| 2011/0245708 A1* | 10/2011 | Finkel | A61B 5/0484 600/544 |
| 2011/0245709 A1* | 10/2011 | Greenwald | A61B 5/048 600/544 |
| 2012/0191000 A1* | 7/2012 | Adachi | A61B 5/048 600/544 |
| 2012/0253213 A1 | 10/2012 | Wei et al. | |
| 2013/0178757 A1* | 7/2013 | Linderman | A61B 5/0488 600/544 |
| 2013/0317380 A1* | 11/2013 | Liley | A61B 5/0476 600/544 |
| 2014/0031712 A1* | 1/2014 | Herskovitz | A61B 5/048 600/545 |
| 2014/0148657 A1* | 5/2014 | Hendler | A61B 5/0478 600/301 |
| 2014/0171757 A1* | 6/2014 | Kawato | A61B 5/0484 600/301 |
| 2015/0073294 A1* | 3/2015 | Zhang | A61B 5/0476 600/544 |
| 2015/0079560 A1* | 3/2015 | Cowan | A61B 5/742 434/236 |
| 2015/0126892 A1* | 5/2015 | Kim | A61B 5/0006 600/545 |
| 2015/0216437 A1* | 8/2015 | Mihajlovic | A61B 5/04012 600/545 |
| 2015/0272465 A1* | 10/2015 | Ishii | A61B 5/0482 600/545 |
| 2015/0272496 A1* | 10/2015 | Klappert | A61B 5/7267 600/545 |

FOREIGN PATENT DOCUMENTS

| | | |
|---|---|---|
| CN | 103300847 A | 9/2013 |
| EP | 1972273 A2 | 9/2008 |
| JP | H08191806 A | 7/1996 |
| JP | 3830156 B1 | 10/2006 |
| JP | 2006280421 A | 10/2006 |

OTHER PUBLICATIONS

International Search Report for PCT/JP2014/078058 dated Feb. 24, 2015.
Written Opinion of the International Searching Authority for PCT/JP2014/078058 dated Feb. 24, 2015.

* cited by examiner

Example1:

generated EEG (lead O1) by using measured EEG of T3, T4, Cz, and Oz

Example2:

generated EEG (lead O1) by using measured EEG of T3, T4, Cz, and Oz

ELECTROENCEPHALOGRAPH, BRAIN WAVE MEASUREMENT METHOD, BRAIN WAVE MEASUREMENT SYSTEM

CROSS-REFERENCE TO RELATED APPLICATIONS

This application is a national stage application (under 35 U.S.C. § 371) of PCT/JP2014/078058, filed Oct. 22, 2014, which is incorporated herein by reference in its entirety.

TECHNICAL FIELD

The present invention relates to electroencephalogram (EEG) measurement apparatus, electroencephalogram measurement method, and electroencephalogram measurement system, capable of measuring electroencephalogram at locations of scalp where electrodes are attached, and estimating electroencephalogram at locations of scalp where no electrodes are attached.

BACKGROUND ART

There are two categories of electroencephalogram waves. The spontaneous electroencephalogram waves include delta wave (2 to 4 Hz), theta wave (4 to 8 Hz), alpha wave (8 to 13 Hz), beta wave (13 to 30 Hz), gamma wave (30 Hz~), occur only by living without doing anything. The evoked EEG waves caused by exogenous stimuli such as visual, auditory and tactile sense, intrinsic mental events such as expectation, attention, decision making, etc., with special frequency components.

Recently, BCI (brain computer interface) utilizing electroencephalogram (spontaneous electroencephalogram and evoked electroencephalogram) as an input signal is widely developed for interactions between, e.g. robots, cars, etc. and human will.

Generally, EEG measurement uses a number of electrodes, as shown in Japanese Patent Application Laid-Open No. 2006-280421, attached on the scalp of a subject. In particular, when measuring high-resolution electroencephalogram (HEEG), 64 to 200 electrodes will be attached depending on applications (see FIG. 2).

SUMMARY OF THE INVENTION

Problem to be Solved by the Invention

However, in order to measure HEEG, it is an obstacle to practical applications of BCI to attach a large number of electrodes of, for example, 64 to 200 on the subject's scalp. In order to make BCI practical, it is necessary to be able to measure or estimate high-resolution electroencephalograms with fewer electrodes.

The present invention has been made in order to eliminate obstacles to practical application of BCI. It is an object of the present invention to provide an electroencephalogram measuring apparatus, an electroencephalogram measurement method, and an electroencephalogram measuring system capable of measuring electroencephalogram waves at locations where electrodes are attached, and estimating an electroencephalogram waves at locations where electrodes are not attached, so that acquiring high-resolution electroencephalogram with a smaller number of electrodes than usual.

In order to achieve the above object, the electroencephalogram measurement apparatus, according to the present invention, includes a plurality of electrodes and an electroencephalogram generation unit.

The plurality of electrodes are attached on the scalp of the subject and acquire the electroencephalogram signals of the subject. An electroencephalogram generation unit generates electroencephalogram on locations where the electrodes are attached and electroencephalogram on locations where the electrodes are not attached by using the electroencephalogram signals acquired from the plurality of electrodes.

According to another aspect of the present invention, there is provided an electroencephalogram measurement method comprising: attaching a plurality of electrodes on the scalp of a subject; and acquiring an electroencephalogram signals of the subject from the plurality of electrodes, and generating electroencephalogram on locations where the electrodes are attached and electroencephalogram on locations where the electrodes are not attached by using the electroencephalogram signals acquired from the plurality of electrodes.

Furthermore, in order to achieve the above object, the electroencephalogram measurement system according to the present invention is an electroencephalogram measurement system in which there are a plurality of the electroencephalogram measurement apparatuses described above connected to each other via a connection line (wired or wireless), a personal coefficient database provided on the cloud, and an electroencephalogram generation unit provided in each electroencephalogram measurement apparatus.

The personal coefficient database is provided on a cloud connected to connection lines (wired or wireless) and stores personal coefficients which are personal specific coefficients generated from electroencephalogram signals acquired from a subject in order to generate an electroencephalogram of the subject.

An electroencephalogram generation unit of each electroencephalogram measurement apparatus generates electroencephalograms on locations where the electrodes are not attached based on the electroencephalogram signals obtained from a plurality of electrodes and the personal coefficient stored in the personal coefficient storage unit or the personal coefficient database on the cloud, if there is personal coefficients that match the information of the subject inputted from the subject information input unit.

On the other hand, when there is no personal coefficient matching the information of the subject, the electroencephalogram on the locations where the electrodes are not attached are calculated based on the electroencephalogram signals acquired from the plurality of electrodes and the group coefficient in the group coefficient storage unit in the electroencephalogram measurement apparatus.

Effect of the Invention

With the electroencephalogram measurement apparatus and electroencephalogram measurement method of the present invention, it is able to generate electroencephalograms at locations where no electrodes are attached by using electroencephalogram signals acquired from a plurality of electrodes, so that with fewer electrodes it is able to generate electroencephalogram with high resolution.

Further, with the electroencephalogram measurement system of the present invention, it is able to generate electroencephalograms at locations where no electrodes are attached by using personal coefficients or group coefficients, so that electroencephalogram of high resolution can be generated with fewer electrodes.

As a result, it is possible to contribute greatly to commercialization of BCI.

DETAILED DESCRIPTION OF EMBODIMENTS

Figure 1:
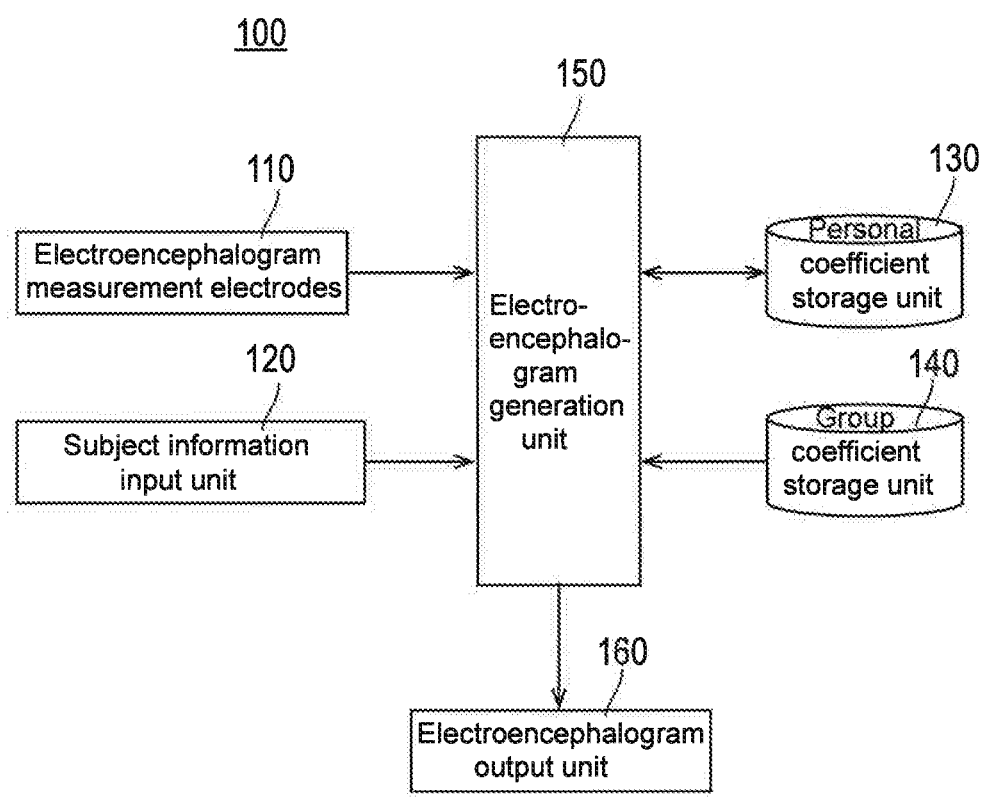
FIG. 1 is a block diagram of an electroencephalogram measurement apparatus according to the present embodiment.

An electroencephalogram measurement apparatus and an electroencephalogram measurement method according to an embodiment of the present invention will be described in detail below with reference to the drawings. FIG. 1 is a block diagram of an electroencephalogram measurement apparatus according to this embodiment.

(Configuration of EEG Measurement Apparatus)

The electroencephalogram measurement apparatus 100 includes electroencephalogram measurement electrodes 110, a subject information input unit 120, a personal coefficient storage unit 130, a group coefficient storage unit 140, an electroencephalogram generation unit 150, and an electroencephalogram output unit 160.

The electroencephalogram measurement electrodes (electrodes) 110 are attached on the scalp of the subject to acquire electroencephalogram signals of the subject. For example, when the International 10-20 system is used, the electroencephalogram measurement electrodes 110 are attached on some locations surrounded by the circles (for example, F7, Cz, P4, etc.) shown in FIG. 4 watching the subject from overhead.

The subject information input unit 120 inputs information of the subject. The information of the subject is personal information such as subject ID, sex, age, name, insurance number. Other information, like home address may also be used. The subject's information is used for identifying the personal coefficients and group coefficients described next.

The personal coefficient storage unit 130 stores personal coefficients that are characteristic coefficients of a subject generated from electroencephalogram signals acquired from the subject, or characteristic electroencephalogram component coefficients generated from each electroencephalogram component. Personal electroencephalogram coefficients or personal electroencephalogram component coefficients are stored for each subject or for each component of the electroencephalogram.

The personal coefficients is specified by the personal information of the subject inputted from the subject information input unit 120. The electroencephalogram component may be, for a spontaneous electroencephalogram, delta wave (2 to 4 Hz), theta wave (4 to 8 Hz), alpha wave (8 to 13 Hz), beta wave (13 to 30 Hz), gamma wave (30 Hz to 30 Hz), and may be, for evoked electroencephalogram, electroencephalogram by exogenous stimuli, such as visual, auditory, or tactile stimuli, and may be electroencephalogram by intrinsic mental events such as expectation, attention, with characteristic frequency component.

Therefore, for example, the personal coefficients are stored for each subject and for each electroencephalogram component of the subject, such as the alpha wave of the subject A and the special frequency component of the subject B. The personal coefficients are stored in association with the personal information of the subject, that is, the subject ID, subject gender, subject age, name, and insurance number. Therefore, by inputting the information of the subject from the subject information input unit 120, it is able to acquire the personal coefficients of the subject from the personal coefficient storage unit 130.

The personal coefficients are coefficients for generating an electroencephalogram at locations where the electroencephalogram measurement electrodes 110 are not attached, by using the electroencephalogram signals actually measured by the electroencephalogram measurement electrodes 110 attached to the subject.

As shown in the following mathematical expression 1, the electroencephalogram signals actually measured by the electroencephalogram measurement electrodes 110 are defined as measurement lead vector A (a 1, a 2, a 3, . . . , an), the personal coefficients, as coefficients in matrix B (b11, b12, . . . , b1n; 21, b22, . . . , b2n; . . . , bn1, bn2, . . . , bnn), the electroencephalogram signals at the locations where the electroencephalogram measurement electrodes 110 are not attached are defined as generation lead vector C (c1, C2, c3, ..., cn), where n is the total number of electroencephalogram measurement electrodes 110. Not to lose generality, measurement leads and generated leads are included in both A and B in Equation 1. Therefore, if let i be a measurement lead, then $c_i$=0, and if let j a generation lead (non-measurement lead), then $a_j$=0.

The generation lead vector C(c1, c2, c3, ..., cn) at locations where the electroencephalogram measurement electrodes 110 are not attached are generated by multiplying the measurement lead vector A (a 1, a 2, a 3, ..., an) with the coefficient matrix B (B11, b12, ..., b1n, b2 1, b22, ..., b2n, ..., bn1, bn2, ..., bnn). As described above, by using the coefficient matrix B, it is able to generate an electroencephalogram at locations where the electroencephalogram measurement electrodes 110 are not attached.

$$\underset{\text{vector}}{\underset{\text{generation lead}}{\begin{bmatrix} c1 \\ c2 \\ c3 \\ \vdots \\ cn \end{bmatrix}}} = \underset{\text{coefficient matrix}}{\begin{bmatrix} b11 & b12 & \dots & b1n \\ b21 & b22 & \dots & b2n \\ & & \vdots & \\ bn1 & bn2 & \dots & bnn \end{bmatrix}} \underset{\text{lead vector}}{\underset{\text{measurement}}{\begin{bmatrix} a1 \\ a2 \\ a3 \\ \vdots \\ an \end{bmatrix}}} \quad \text{(Expression 1)}$$

In addition, it is necessary to acquire personal coefficients for each subject and for each EEG component of the same subject. The procedure for acquiring personal coefficients will be described in detail later by using the flowchart of FIG. 3.

In order to generate an electroencephalogram of a subject, the group coefficient storage unit 140 stores values obtained by statistically processing a plurality of personal coefficients acquired from an unspecified large number of people of a statistically effective population as group coefficients. The group coefficients are coefficients used when there is no personal coefficients of the subject. The group coefficients are group coefficients obtained from the whole population consisting of an unspecified large number of people, or population of an unspecified large number of people with grouped with gender, age. These group coefficients are stored as group coefficients of the entire electroencephalogram or group coefficients of each electroencephalogram component.

The electroencephalogram generation unit 150 generates electroencephalograms at locations where the electroencephalogram measurement electrodes 110 are attached and electroencephalograms at locations where the electroencephalogram measurement electrodes 110 are not attached by using the electroencephalogram signals acquired from the plurality of electroencephalogram measurement electrodes 110.

Specifically, when there are a personal coefficients that match the information of the subject inputted from the subject information input unit 120 in the personal coefficient storage unit 130, the electroencephalogram generation unit 150 generates electroencephalograms on locations where no electrodes are attached with the electroencephalogram signals acquired from the plurality of electroencephalogram measurement electrodes 110 and the personal coefficients stored in the personal coefficient storage unit 130.

On the other hand, when there are no personal coefficients that match the subject's information inputted from the subject information input unit 120 in the personal coefficient storage unit 130, the electroencephalogram generation unit 150 generates the electroencephalogram on locations where no electrodes are attached by using the electroencephalogram signals acquired from the plurality of electroencephalogram measurement electrodes 110 and the group coefficients stored in the group coefficient storage unit 140.

The electroencephalogram generation unit 150 generates electroencephalogram of the subject, and if necessary, processes the electroencephalogram signals to generate electroencephalogram components.

The electroencephalogram output unit 160 outputs the electroencephalogram generated by the electroencephalogram generation unit 150. The electroencephalogram output unit 160 can output the electroencephalogram of all locations generated by the electroencephalogram generation unit 150 or a part of locations designated by the electroencephalogram generation unit 150. The electroencephalogram waveforms can be selectively outputted. The electroencephalogram output unit 160 has at least one of functions of outputting electroencephalogram as data to other information processing apparatuses, of printing electroencephalogram waveforms, and of displaying electroencephalograms waveforms on a display.

Figure 2:
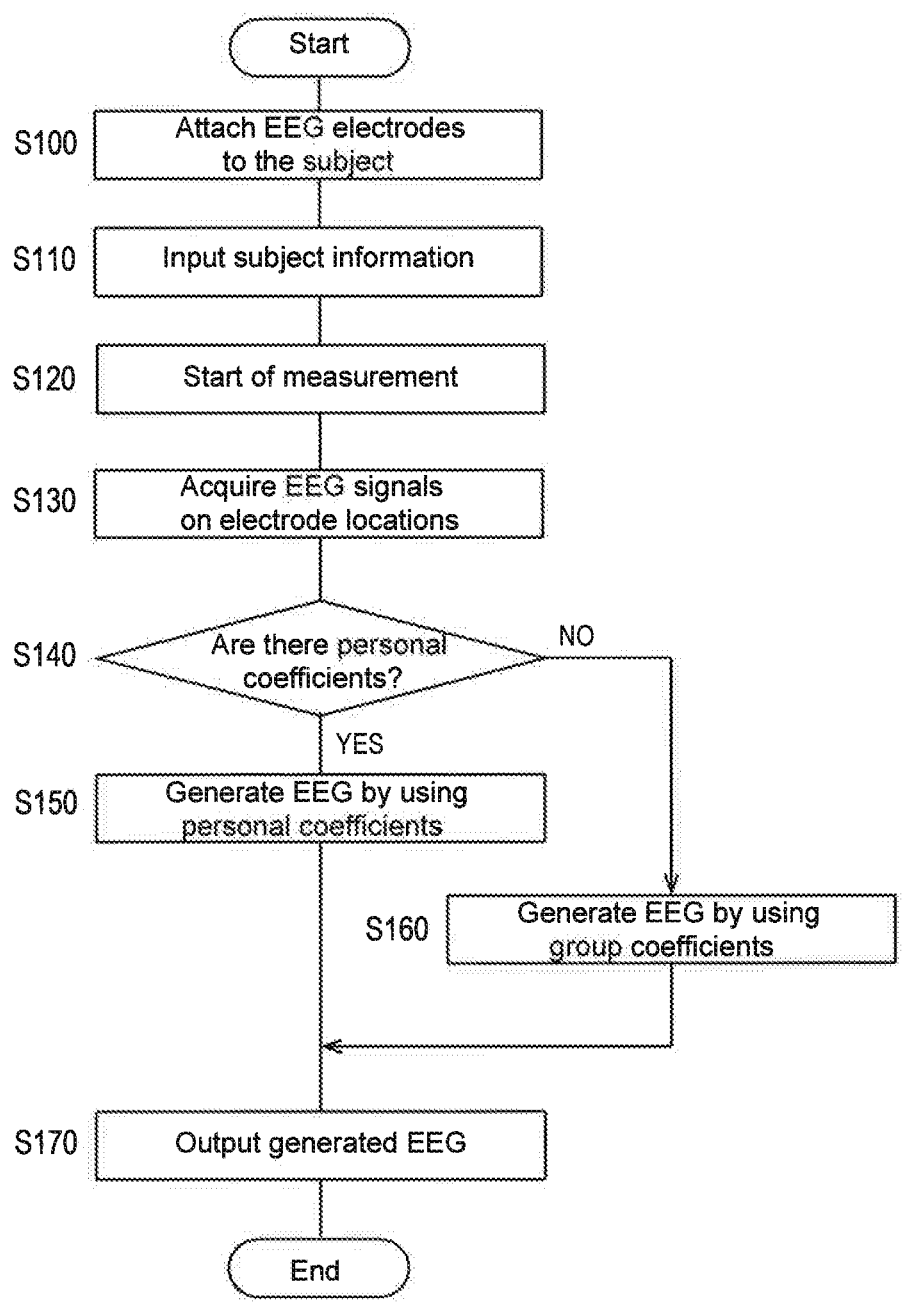
FIG. 2 is a flowchart of an electroencephalogram measurement method according to the present embodiment.

(Operation of Electroencephalogram Measuring Apparatus) FIG. 2 is a flowchart of the electroencephalogram measurement method according to the present embodiment. The flowchart of FIG. 2 is also a flowchart showing the operation of the electroencephalogram measurement apparatus 100 shown in FIG. 1.

Figure 4:
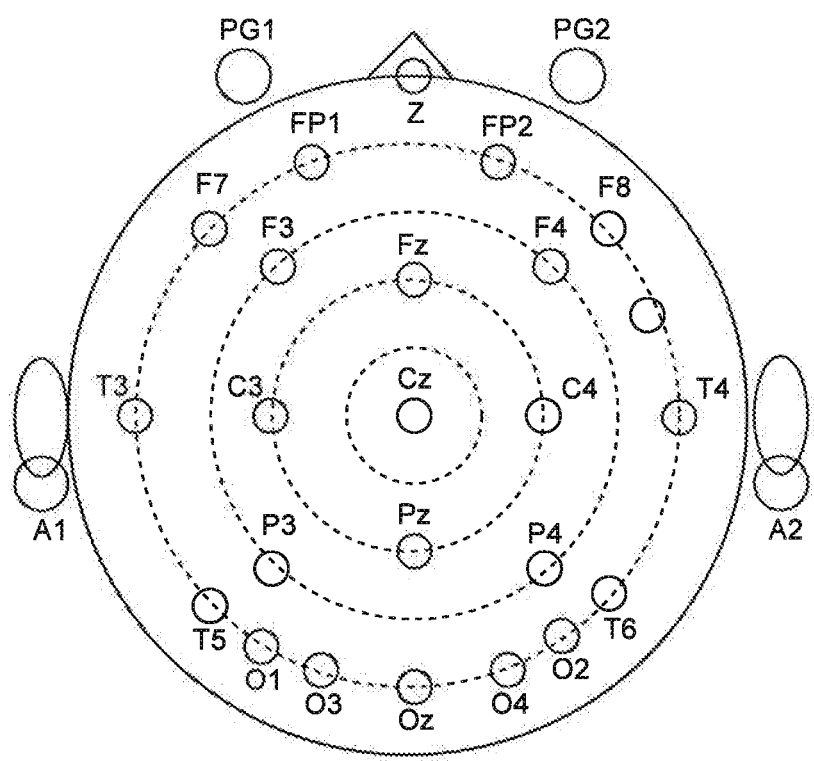
FIG. 4 is a diagram provided for explaining the generation of electroencephalogram.

In the case of measuring an electroencephalogram, first, the electroencephalogram measurement electrodes 110 are attached to the subject (S100). As shown in FIG. 4, the electroencephalogram measurement electrodes 110 are attached on the scalp of the subject as many as required, in the present embodiment, four electrodes are attached to locations indicated by T3, T4, C z, Oz shown in FIG. 4.

Next, information of the subject is inputted from the subject information input unit 120 (S110). The information of the subject is personal information such as subject ID, subject's sex, subject age, name, health number, and the like.

The electroencephalogram generation unit 150 starts measurement of electroencephalogram (S 120).

The electroencephalogram generation unit 150 acquires the electroencephalogram signals from the electroencephalogram measurement electrodes 110 attached to the four locations indicated by T3, T4, Cz, Oz in FIG. 4, and stores the acquired electroencephalogram signals over a certain period of time (S130).

The electroencephalogram generation unit 150 judges whether or not there are personal coefficients for the subject in the personal coefficient storage unit 130 by using the personal information inputted from the subject information input unit 120 (S140). When there are personal coefficients of the subject (S140: YES), electroencephalograms are generated by using the personal coefficients for the subject (S150). On the other hand, when there are no personal coefficients for the subject (S140: NO), the electroencephalogram generation unit 150 generates electroencephalograms by using group coefficients stored in the group coefficient storage unit 140 that match subject's information such as the subjects gender, age (S160). The electroencephalogram components (one or more may be specified) can also be generated this way.

The electroencephalogram generated by the electroencephalogram generation unit 150 is outputted (s170) by the electroencephalogram output unit 160.

The electroencephalogram measurement apparatus 100 generates the electroencephalogram of the subject in the said procedure. When practicing BCI, it is preferable that the number of electrodes to be attached to the subject is minimized as much as possible, but on the other hand it is preferable to be able to acquire electroencephalograms of as many locations as possible. How much number of electroencephalogram measurement electrodes and where the electrodes attached to accurately electroencephalogram can be topics of future research. However, the idea of obtaining high-resolution electroencephalogram with fewer measuring electrodes and using the group coefficients and personal coefficients is proposed for the first time by the electroencephalogram measuring apparatus of the present invention.

Figure 3:
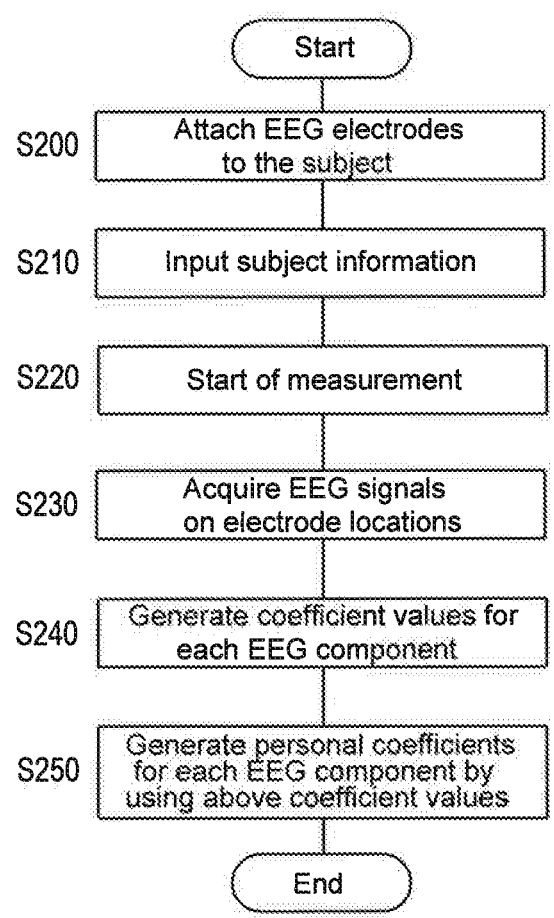
FIG. 3 is a flowchart showing procedures for acquiring personal coefficients.

FIG. 3 is a flowchart showing a procedure for acquiring personal coefficients. FIG. 4 is a diagram for explaining generation of an electroencephalogram.

To acquire the personal coefficients, first, the electroencephalogram measurement electrodes 110 are attached to the subject (S200). The electroencephalogram measurement electrodes 110 are attached to all the necessary locations on the scalp of the subject as shown in FIG. 4. Specifically, when the international 10-20 system as shown in FIG. 4 is used, it is necessary to set to locations of FP1, FP2, F7, F3, Fz, F4, F8, T3, C3, Cz, C4, T4, P3, Pz, P4, T5, O1, O3, Oz, O4, O2, T6. In cases of using HEEG, for example, electroencephalogram measurement electrodes 110 may have a number of electrodes between 64 to 200.

The subject information input unit 120 inputs subject information such as subject's ID, sex, subject age, name, insurance number, and the like.

The electroencephalogram generation unit 150 starts measurement of electroencephalogram (S220).

When the international 10-20 system is used, the electroencephalogram generation unit 150 generates electroencephalograms of 22 points on the scalp of the subject shown in FIG. 4 acquired from the electroencephalogram measurement electrodes 110 and stored for a predetermined period of time (S230).

The electroencephalogram generation unit 150 generates values of coefficients from the obtained electroencephalogram signals or electroencephalogram component acquired (S240).

As shown in expression 1, taken the electroencephalogram signals actually measured by the electroencephalogram measurement electrodes 110 as measurement lead vector A (a 1, a 2, a 3, . . . , an), the personal coefficients, as coefficients in matrix B (b11, b12, . . . , b1n; 21, b22, . . . , b2n; . . . , bn1, bn2, . . . , bnn), the electroencephalogram signals at the location where the electroencephalogram measurement electrodes 110 are not attached as generation lead vector C (c1, C2, c3, . . . , cn), the generation lead vector C can be obtained by multiplying the measurement lead vector A with the coefficient B, where n is the total number of electroencephalogram measurement electrodes 110. Not to lose generality, both measurement leads and generated leads are included in both sides of A and B in Equation 1. It is clear that, if let r be a measurement lead, then $c_r \equiv 0$, and if let j be a generation lead (non-measurement lead), then $a_j = 0$.

To obtain coefficients in matrix B (b11, b12, . . . , b1n, b21, b22, . . . , b2n, . . . , bn1, bn2, . . . , bnn) which is called personal coefficients, the electroencephalogram signals of the measurement lead vector A (a 1, a 2, a 3, . . . , an), and the generation lead vector C (c 1, c 2, c 3, . . . , cn) are measured with time.

The coefficients in matrix B (b11, b12, . . . , b1n, b21, b22, . . . , b2n, . . . , bn1, bn2, . . . , bnn) are obtained by solving equation 1 with measurement lead vector A (a 1, a 2, a 3, . . . , an), as source, and the generation lead vector C (c 1, c2, c3, . . . , cn), as destination, being assigned corresponding electroencephalogram signals of the measured time series. The obtained coefficients are the personal coefficients of the subject.

For an explanation, the coefficients actually reflect relationship between the electroencephalogram signals acquired by the electroencephalogram measurement electrode 110 at 22 locations shown in FIG. 4, for example, relationship between the electroencephalogram signals acquired by the electroencephalogram measurement electrode 110 at 22 locations and the electroencephalogram signal acquired by the electroencephalogram measurement electrode 110 at the location of Cz, or, relationship between the electroencephalogram signals acquired by the electroencephalogram measurement electrode 110 at 22 locations and the electroencephalogram signal acquired by the electroencephalogram measurement electrode 110 at the location of C4, and etc.

In this way, the coefficients in matrix B inherent to the subject is obtained by finding the relationship between the electroencephalogram signals acquired by the electroencephalogram measurement electrode 110 at a part of all locations and the electroencephalogram signals acquired by the electroencephalogram measurement electrodes 110 at all other locations.

The electroencephalogram generation unit 150 obtains personal coefficients of the subject for electroencephalogram itself, or electroencephalogram components, from the calculated value of the coefficients in matrix B (S250). It is noted that the precision for generating electroencephalogram is not significantly changed, whether personal coefficients are generated from the recorded raw waveform or for each electroencephalogram component. The electroencephalogram components may be components such as delta wave (2 to 4 Hz), theta wave (4 to 8 Hz), alpha wave (8 to 13 Hz), beta wave (13 to 30 Hz), gamma wave (30 Hz~), caused by spontaneous electroencephalogram, or electroencephalogram components caused by exogenous stimulation such as visual, auditory, tactile sense, or an intrinsic mental event such as expectation, attention, decision making, etc. All these components have special frequencies.

FIGS. 5 to 8 show examples of the electroencephalograms generated by the electroencephalogram measurement apparatus 100 of the present embodiment.

Figure 5:
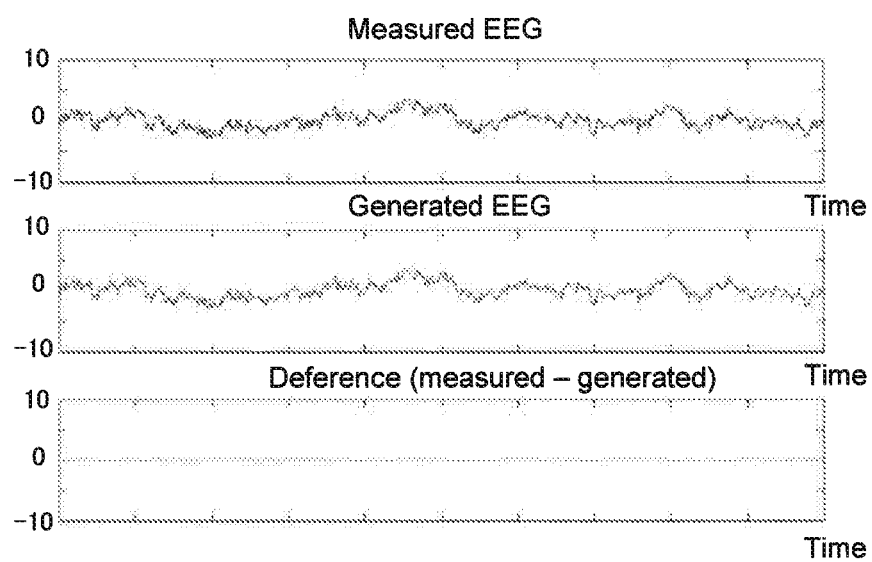
FIG. 5 is an example of a generated electroencephalogram.

FIG. 5 shows one example. The electroencephalogram (actually measured electroencephalogram) is measured by attaching the electroencephalogram measurement electrodes 110 to location 01 (zero 1) in FIG. 4, and four other locations of T3, T4, Cz, and Oz (not shown in this figure). The measured raw electroencephalograms are preprocessed with a bandpass filter (0.5-40 Hz), and the noise is eliminated. First, with respect to preprocessed electroencephalograms, personal coefficients for generating electroencephalograms at the location of 01 are obtained by calculation from four electroencephalograms of 01 and T3, T4, Cz, and Oz in a certain period of time. Using the personal coefficients thus obtained, electroencephalogram of the location of 01 are generated from the four electroencephalograms T3, T4, Cz, and Oz in a period of time different from the period of time when the personal coefficients are obtained. The waveform on the upper row in FIG. 5 is a measured waveform at the location of 01, the electroencephalogram generated by using the personal coefficient is showed in the middle row, and on the lower row is shown difference between the measured electroencephalogram and the generated electroencephalogram.

As can be seen from FIG. 5, the measured waveform is very close to the generated waveform. Looking at the difference, it is almost 0. From this figure, it can be seen that the electroencephalogram measurement apparatus 100 can very accurately generate electroencephalograms at locations where the electroencephalogram measurement electrodes 110 are not attached.

Figure 6:
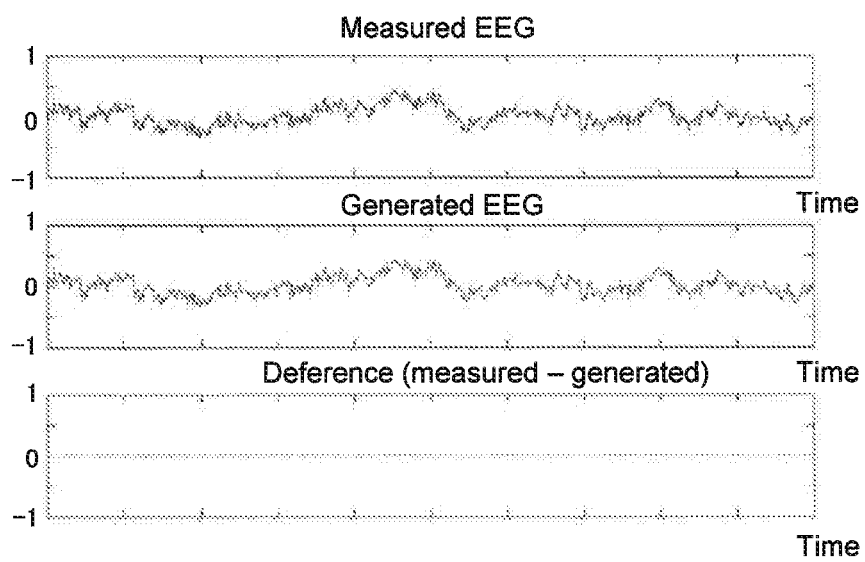
FIG. 6 is an example of a generated electroencephalogram.

FIG. 6 shows a second example of electroencephalogram generation. The electroencephalograms are measured by attaching the electroencephalogram measurement electrodes 110 to the location of 01 (zero 1) in FIG. 4, and other four locations of T3, T4, Cz, and Oz in the figure. The measured raw electroencephalograms are pre-processed with a band pass filter in the band of alpha wave (8 to 13 Hz) to extract the alpha wave component. For the electroencephalogram component of the alpha wave, first, in a period of time, personal coefficients for generation of an electroencephalogram of the alpha wave component at the location of 01 is generated from electroencephalogram of 01 and T3, T4, Cz, and Oz. Using the personal coefficients obtained in this way, from the four alpha wave components of T3, T4, Cz, and Oz in a period of different time when the personal coefficient was obtained, the alpha wave of electroencephalogram on location 01 was generated. The upper graph of FIG. 6 shows alpha wave actually measured, the middle row shows alpha wave generated by using personal coefficients and alpha waves on other four locations of T3, T4, Cz, and Oz, and the lower row shows the difference between the upper and middle waveforms.

As can be seen from FIG. 6, the measured waveform is very close to the generated waveform. Looking at the difference, it is almost 0. From this figure, it can be seen that the electroencephalogram measurement apparatus 100 can very accurately generate electroencephalograms at locations where the electroencephalogram measurement electrodes 110 are not attached.

Figure 7:
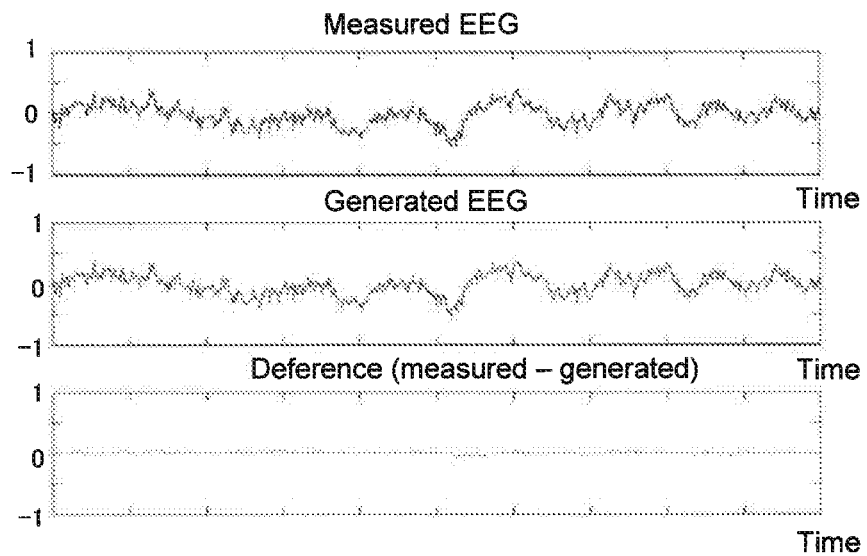
FIG. 7 is an example of a generated electroencephalogram.

FIG. 7 shows a third example of electroencephalogram generation. The electroencephalograms are measured by attaching the electroencephalogram measurement electrodes 110 to the location of 01 (zero 1) in FIG. 4, and at other four locations of T3, T4, Cz, and Oz in the figure. The measured raw electroencephalograms are pre-processed with a band pass filter in the band of beta wave (14 to 30 Hz) to extract the beta wave component. For the electroencephalogram component of the beta wave, first, in a period of time, personal coefficients for generation of an electroencephalogram of the beta wave component at the location of 01 is generated from electroencephalograms of 01 and T3, T4, Cz, and Oz. Using the personal coefficients obtained in this way, from the four beta wave components of T3, T4, Cz, and Oz in a period of time different from the time when the personal coefficient was obtained, the beta wave of electroencephalogram on location 01 was generated. The upper graph of FIG. 7 shows beta wave actually measured, the middle row shows beta wave generated by using personal coefficients and beta waves on other four locations of T3, T4, Cz, and Oz, and the lower row shows the difference between the upper and middle waveforms.

As can be seen from FIG. 7, the measured waveform is very close to the generated waveform. Looking at the difference, it is almost 0. From this figure, it can be seen that the electroencephalogram measurement apparatus 100 can very accurately generate electroencephalograms at locations where the electroencephalogram measurement electrodes 110 are not attached.

Figure 8:
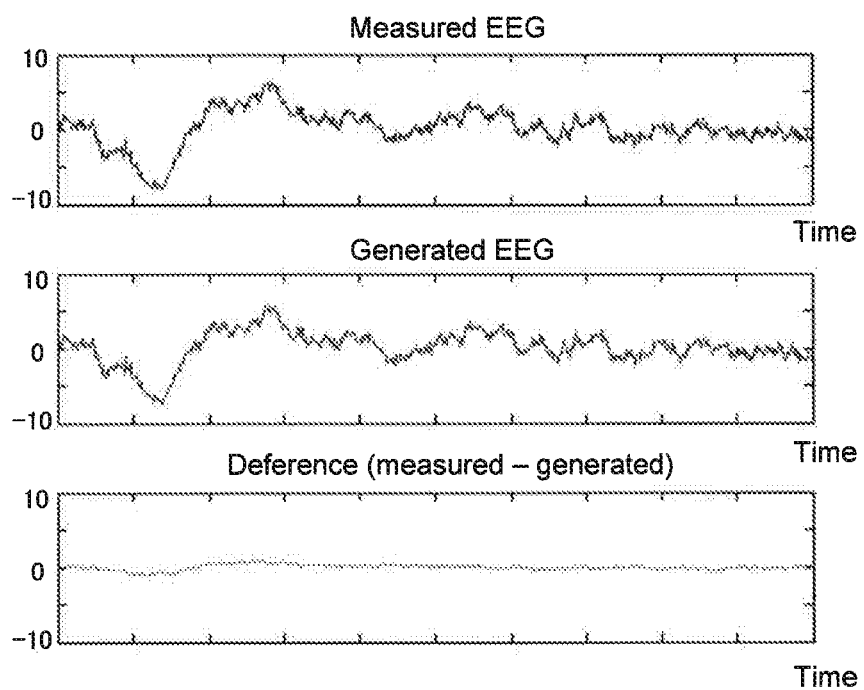
FIG. 8 is an example of a generated electroencephalogram.

FIG. 8 shows one more generation example. Electroencephalograms are measured by attaching the electroencephalogram measurement electrodes 110 to the location of 01 (zero 1) shown in FIG. 4, and other four locations of T3, T4, Cz, and Oz in the figure. The measured raw electroencephalograms are preprocessed with a bandpass filter (0.5-40 Hz), and the noise is eliminated. The electroencephalogram at the location of 01 is also generated from the four electroencephalograms of T3, T4, Cz, and Oz by using the personal coefficients obtained from other subject. The waveform in the upper row of FIG. 8 is a measured waveform at the location of 01, the middle row shows the waveform generated by using the personal coefficients of other persons, and the lower row shows the difference between the actually measured electroencephalogram and the generated electroencephalogram.

FIG. 8 is different from FIG. 5 in that it used an personal coefficient of another person instead of its own personal coefficient to generate electroencephalogram at the location of 01. As can be seen from FIG. 8, the measured electroencephalogram is very close to the generated electroencephalogram. Although the difference is small, but slightly higher than that in FIG. 5. To use the personal coefficients of others is an extreme case where there is only one sample in the group for which group coefficients are solved. Even though, the accuracy of the generated electroencephalogram is still high. From this figure, it can be seen that the electroencephalogram measurement apparatus 100 can very accurately generate electroencephalograms at locations where the electroencephalogram measurement electrodes 110 are not attached.

As shown above, the electroencephalogram measurement apparatus and the electroencephalogram measurement method according to the present embodiment are able to generate with high accuracy the electroencephalograms from electroencephalograms on locations where the electroencephalogram measurement electrodes 110 actually attached for the locations where the electroencephalogram measurement electrodes 110 are not attached.

Therefore, the electroencephalogram measuring apparatus and the electroencephalogram measurement method according to the present embodiment are able to measure electroencephalograms of high resolution with fewer electrodes, which can greatly contribute to commercialization of BCI.

Figure 9:
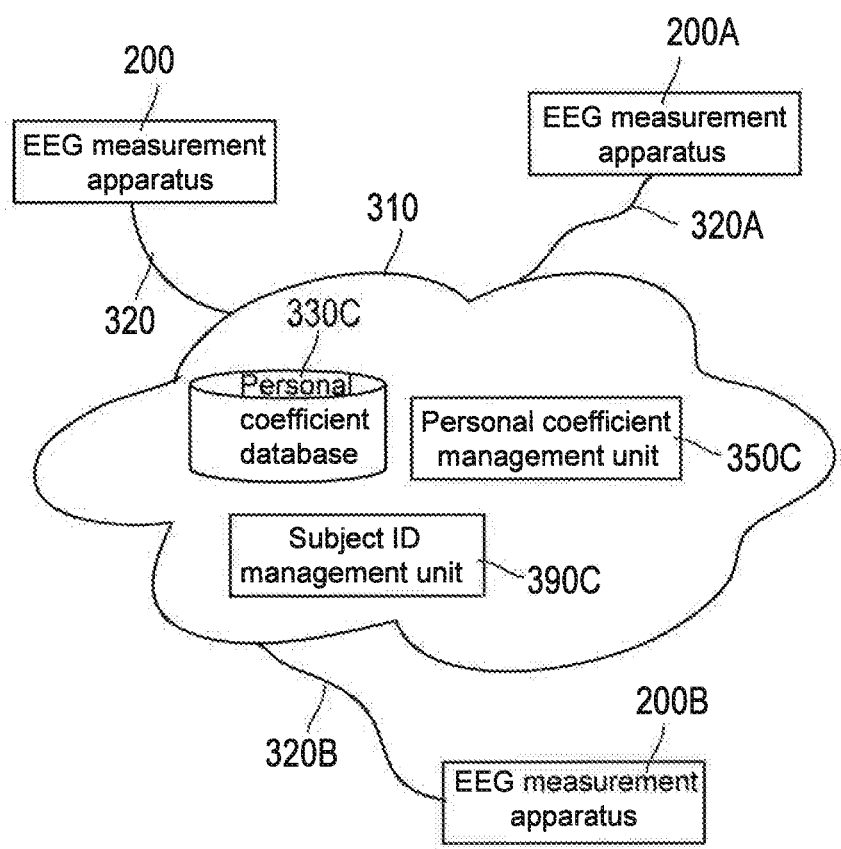
FIG. 9 is a block diagram of an electroencephalogram measurement system according to this embodiment.

Next, an electroencephalogram measurement system according to the embodiment of the present invention will be described in detail with reference to the drawings. FIG. 9 is a block diagram of an electroencephalogram measurement system according to this embodiment.

(Configuration of Electroencephalogram Measurement System)

The electroencephalogram measurement system 300 according to the present embodiment includes an personal coefficient database 330C, an personal coefficient management unit 350C, and a subject ID management unit 390C provided on the electroencephalogram measurement apparatuses 200, 200A, and 200B and the cloud 310. The said electroencephalogram measurement apparatuses 200, 200A, and 200B are connected to the cloud 310 via connection lines 320, 320A, 320B (wired or wireless). In the present embodiment, there are three electroencephalogram measurement apparatuses, but in fact it is possible to provide an unspecified number of electroencephalogram measurement apparatuses in measurement locations in an unspecified manner.

Compared with the electroencephalogram measurement apparatus 100 shown in FIG. 1, the electroencephalogram measurement apparatuses 200, 200A, and 200B have a function for communicating with the cloud 310, a function for searching for personal coefficients of the subject on the cloud 310, and a function of obtaining the personal coefficients of the subject and storing it on the cloud 310. The electroencephalogram measurement apparatuses 200, 200A, and 200B incorporate a program for exerting these functions. Detailed configurations of the electroencephalogram measurement apparatuses 200, 200A, and 200B will be described later in details.

The cloud 310 may be a data center provided by a cloud provider. The data center is provided with a personal coefficient database 330C, a personal coefficient management unit 350 C, and a subject ID management unit 390C. In the present embodiment, the personal coefficient management unit 350 C and the subject ID management unit 390C are provided on the cloud 310, but these may be provided outside the cloud 310.

Connection lines (wired or wireless) 320, 320A, and 320B connect the electroencephalogram measurement apparatuses 200, 200A, and 200B to the cloud 310. The connection lines 320, 320A, 320B may be wired or wireless dedicated lines connecting the electroencephalogram measurement apparatuses 200, 200A, 200B and the cloud 310, or may be a wired or wireless internet connections with security configurations.

The personal coefficient database 330C stores personal coefficients of all subjects generated by all the electroencephalogram measurement apparatuses 200, 200A, and 200B connected to the cloud 310. The personal coefficients are stored in association with a unique ID given to each subject exactly one worldwide. All the electroencephalogram measurement apparatuses 200, 200A, 200B are allowed to access to the personal coefficient database 330C. All of the electroencephalogram measurement apparatuses 200, 200A, 200B can store the generated personal coefficients in the personal coefficient database 330C or can refer to personal coefficients stored in the personal coefficient database 330C.

The personal coefficient management unit 350C manages access to all the electroencephalogram measurement apparatuses 200, 200A, and 200B to the personal coefficient database 330C. The detailed configuration and operation of the personal coefficient management unit 350 C will be described later.

The subject ID management unit 390C has a function of converting the same subject's ID into subject IDs used in the electroencephalogram measurement apparatuses 200, 200A, 200B, which is used when the electroencephalogram measurement apparatuses 200, 200A, and 200E placed at unspecified measurement locations retrieve personal coefficients of a specific subject. For example, when a subject ID "A123" is attached to the electroencephalogram measurement apparatus 200 and a subject ID "B456" is attached to the electroencephalogram measurement apparatus 200A, for the same subject, "A123" and "B456" for the same subject should be converted to each other. A unique ID is used for conversion of the subject ID between the electroencephalogram measurement apparatuses. The unique ID is an ID given to the subject exactly one world. This ID is unique to that subject commonly usable by any electroencephalogram measuring apparatus in the world, so that double registration cannot be performed for the same subject. The subject ID managing unit 390C has a lookup table of unique IDs and subject IDs, and the lookup table is constantly updated according to requests from the electroencephalogram measurement apparatuses 200, 200A, and 200B.

Figure 10:
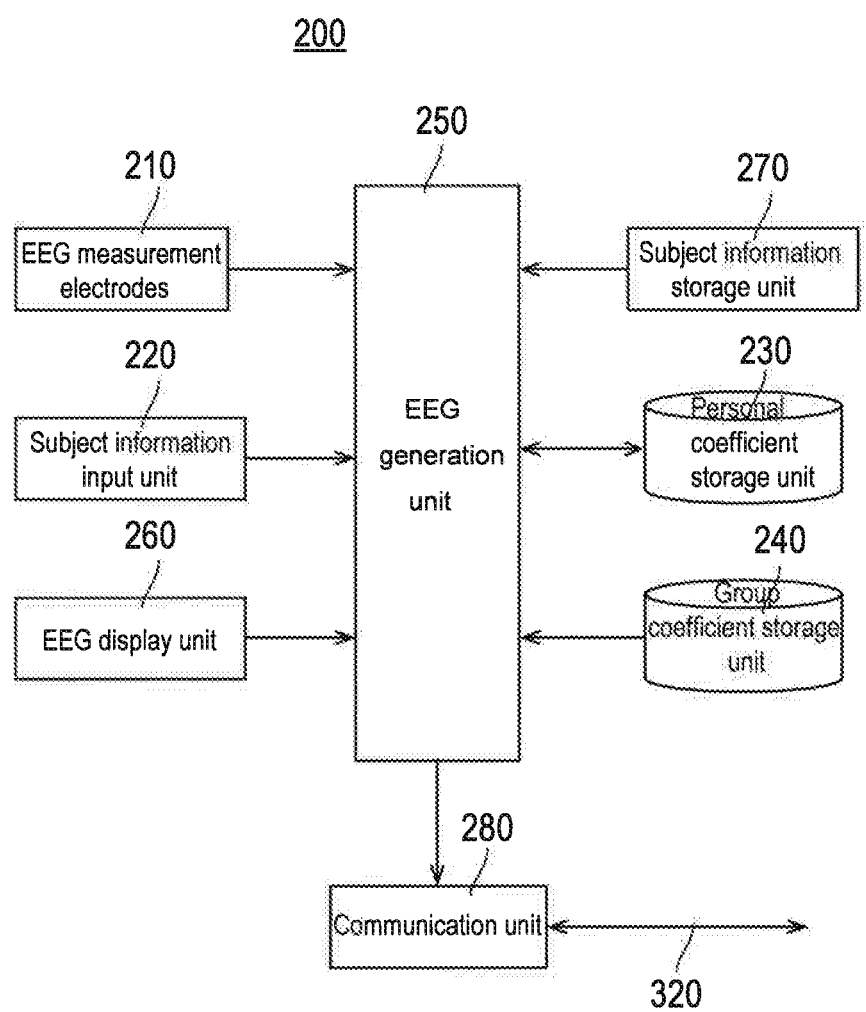
FIG. 10 is a block diagram of an electroencephalogram measurement apparatus in an electroencephalogram measurement system.

FIG. 10 is a block diagram of the electroencephalogram measurement apparatus 200 in the electroencephalogram measurement system 300.

[Configuration of Electroencephalogram Measurement Apparatus]

The electroencephalogram measurement apparatus 200 includes electroencephalogram measurement electrodes 210, a subject information input unit 220, a personal coefficient storage unit 230, a group coefficient storage unit 240, an electroencephalogram generation unit 250, an electroencephalogram display unit 260, a subject information storage unit 270, and a communication unit 280.

The electroencephalogram measurement electrodes 210, the subject information input unit 220, the personal coefficient storage unit 230, the group coefficient storage unit 240, and the electroencephalogram generation unit 250 of the electroencephalogram measurement apparatus 200 are the same as those of the electroencephalogram measurement apparatus 100, the measurement electrode 110, the subject information input unit 120, the personal coefficient storage unit 130, the group coefficient storage unit 140, and the electroencephalogram generation unit 150 as shown in FIG. 1.

The subject information storage unit 270 stores information on the subject inputted by the subject information input unit 220. The information of the subject is personal information such as subject's ID, sex, age, name, insurance number, and the like.

The communication unit 280 communicates with cloud 310 via a connection line (wired or wireless) 320.

Figure 11:
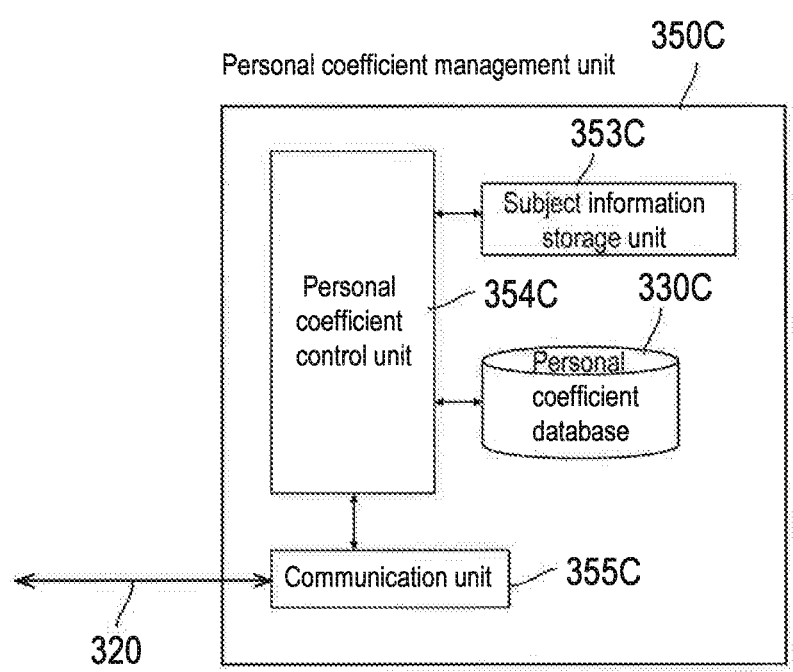
FIG. 11 is a block diagram of a personal coefficient management unit in an electroencephalogram measurement system.

FIG. 11 is a block diagram of the personal coefficient management unit 350 C in the electroencephalogram measurement system 300.

[Configuration of Personal Coefficient Management Unit]

The personal coefficient management unit 350 C has a personal coefficient database 330C, a subject information storage unit 353C, a personal coefficient control unit 354C, and a communication unit 355C.

The personal coefficient database 330C stores the same personal coefficients in the personal coefficient storage units in the electroencephalogram measurement apparatuses 200, 200A, 200B (the personal coefficient storage unit 230 in case of the electroencephalogram measurement apparatus 200). The personal coefficient database 330C collectively stores all the personal coefficients of all the electroencephalogram measurement apparatuses 200, 200A, and 200B connected to the cloud 310. The personal coefficients stored in the personal coefficient database 330C are associated with the subject's unique ID.

The subject information storage unit 353C stores the same subject information as the subject information stored in the subject information storage units in the electroencephalogram measurement apparatuses 200, 200A, and 200B (the subject information storage unit 270 in case of the electroencephalogram measurement apparatus 200). The subject information storage unit 353C collectively stores all the subject information of all the electroencephalogram measurement apparatuses 200, 200A, and 200B connected to the cloud 310.

The personal coefficient control unit 354C comprehensively controls the operation of the personal coefficient management unit 350C. The personal coefficient control unit 354C has a function of enabling information of the subject stored in the subject information storage unit 353C, a function of enabling the personal coefficient of the subject stored in the personal coefficient database 330C, or enabling personal coefficients retrieved from the personal coefficient database 330C. The detailed operation of the personal coefficient manager 350C will be described later.

The communication unit 355C receives the subject information and the personal coefficients from the electroencephalogram measurement apparatuses 200, 200A, and 200B. It transmits personal coefficients to the electroencephalogram measurement apparatuses 200, 200A, and 200B. It transmits the subject ID to the subject ID management unit 390C, and receives the converted subject ID. The subject information, subject ID and personal coefficients are transmitted and received via connection line 320.

Figure 12:
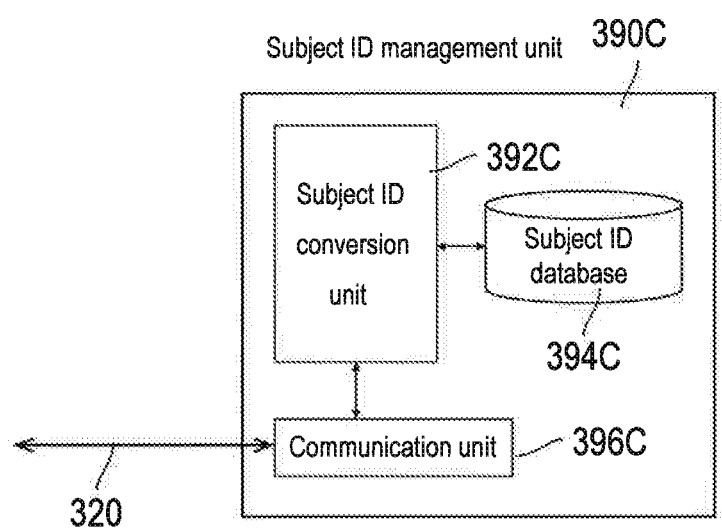
FIG. 12 is a block diagram of a subject ID management unit in an electroencephalogram measurement system.

FIG. 12 is a block diagram of the subject ID management unit 390C in the electroencephalogram measuring system 300.

[Configuration of Subject ID Management Unit]

The subject ID management unit 390C includes a subject ID database 394C, a subject ID converting unit 392C, and a communication unit 396C.

The subject ID database 394C stores the subject's unique ID and subject ID in association with each other. For example, if the unique ID of the subject is "C123", the subject ID inputted by the electroencephalogram measurement apparatus 200 is "A123", and the subject ID inputted by the electroencephalogram measurement apparatus 200A is "B456", then "C123"-"A123", "C123"-"B456" are stored.

The subject ID converting unit 392C refers to the unique ID of the subject and converts it into the subject ID of the subject stored in each of the electroencephalogram measurement apparatuses 200, 200A, and 200B.

For example, when the electroencephalogram measurement apparatus 200 is going to search for the personal coefficient of the subject registered by the electroencephalogram measurement apparatus 200A, the subject ID database 394C is accessed by relying on the unique ID "C123", and the subject ID "A123" of the subject inputted by the electroencephalogram measurement apparatus 200 is converted into the subject ID "B456" of the subject inputted by the electroencephalogram measurement apparatus 200A.

The communication unit 396C receives the subject ID of the subject transmitted from the electroencephalogram measurement apparatuses 200, 200A, and 200B, and transmits the subject ID converted by the subject ID conversion unit 392C to the electroencephalogram measurement apparatuses 200, 200A, and 200B.

Next, the operation of the electroencephalogram measurement system 300 according to this embodiment will be described with reference to the FIGS. 13 through 21. The operation that overlaps the operation of the electroencephalogram measurement apparatus 100 shown in FIG. 1 will be described briefly.

(Operation of Electroencephalogram Measurement System)

Figure 13:
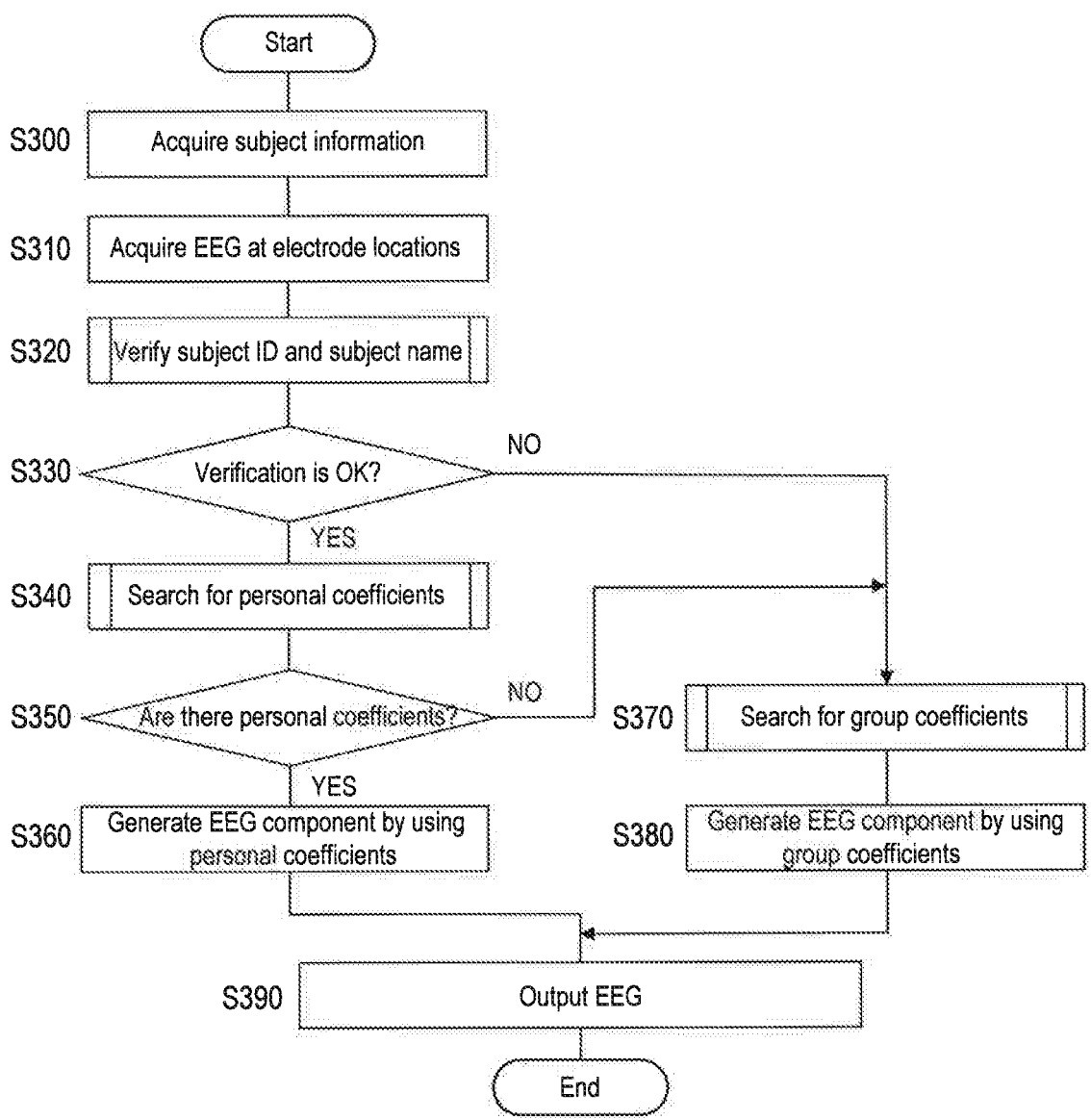
FIG. 13 is a main flowchart showing the processing of the electroencephalogram measurement system according to this embodiment.

FIG. 13 is a main flowchart showing processing of the electroencephalogram measurement system 300 according to the present embodiment. This main flowchart is processed by the electroencephalogram generation unit 250 of the electroencephalogram measurement apparatus 200.

The electroencephalogram generation unit 250 acquires information on the subject inputted from the subject information input unit 220 (step S300), Information on the subject is the subject ID, gender, age, name, insurance number, etc. The subject ID and subject name are used when retrieving the personal coefficients of the subject. The subject's age and gender are used when searching for group coefficients.

The electroencephalogram generation unit 250 acquires the electroencephalogram signals from the plurality of electroencephalogram measurement electrodes 210 attached to the scalp of the subject (step S310).

The electroencephalogram generation unit 250 exams the "subject ID and subject name" stored in the subject information storage unit 270 or subject information storage unit 353C (Step S320).

If there is "subject ID and subject name" that match the subject information storage unit 353C, it is verified OK (step S330: YES), then the personal coefficients stored in the personal coefficient storage unit 230 or personal coefficient database 330C are searched.

If there is a personal coefficients of the subject in the personal coefficient storage unit 230 or in the personal coefficient database 330C (step S350: YES), the electroencephalogram generation unit 250 reads from the personal coefficient storage unit 230 or the personal coefficient database 330C to get personal coefficients. The electroencephalogram generation unit 250 then generates electroencephalograms, or electroencephalogram components by using the electroencephalogram signals acquired by the plurality of electroencephalogram measurement electrodes 210 and the obtained personal coefficients (step S360).

Here by electroencephalogram component, it may mean spontaneous electroencephalograms such as delta wave (2 to 4 Hz), theta wave (4 to 8 Hz), alpha wave (8 to 13 Hz), beta wave (13 to 30 Hz), gamma wave (30 Hz-), or an evoked electroencephalogram caused by an exogenous stimulus such as visual, auditory, or tactile stimuli, or an intrinsic mental event such as expectation, attention, decision making, or the like.

On the other hand, when there is no "subject ID and subject name" matching the subject information storage unit 270 or the subject information storage unit 353C (step S330: NO), or when the personal coefficient storage unit 230 (S350: No), the electroencephalogram generation unit 250 searches for the group coefficients stored in the group coefficient storage unit 240. The electroencephalogram generation unit 250 obtains an optimum group coefficient for the subject from the group coefficient storage unit 240 by looking at the age and sex of the subject (step S370).

The electroencephalogram generation unit 250 uses the electroencephalogram signals detected by the plurality of electroencephalogram measurement electrodes 210 and the acquired group coefficients to generate electroencephalograms or electroencephalogram components (step S380).

The electroencephalogram generation unit 250 outputs the generated electroencephalogram to the electroencephalogram display unit 260 (step S390).

Figure 14:
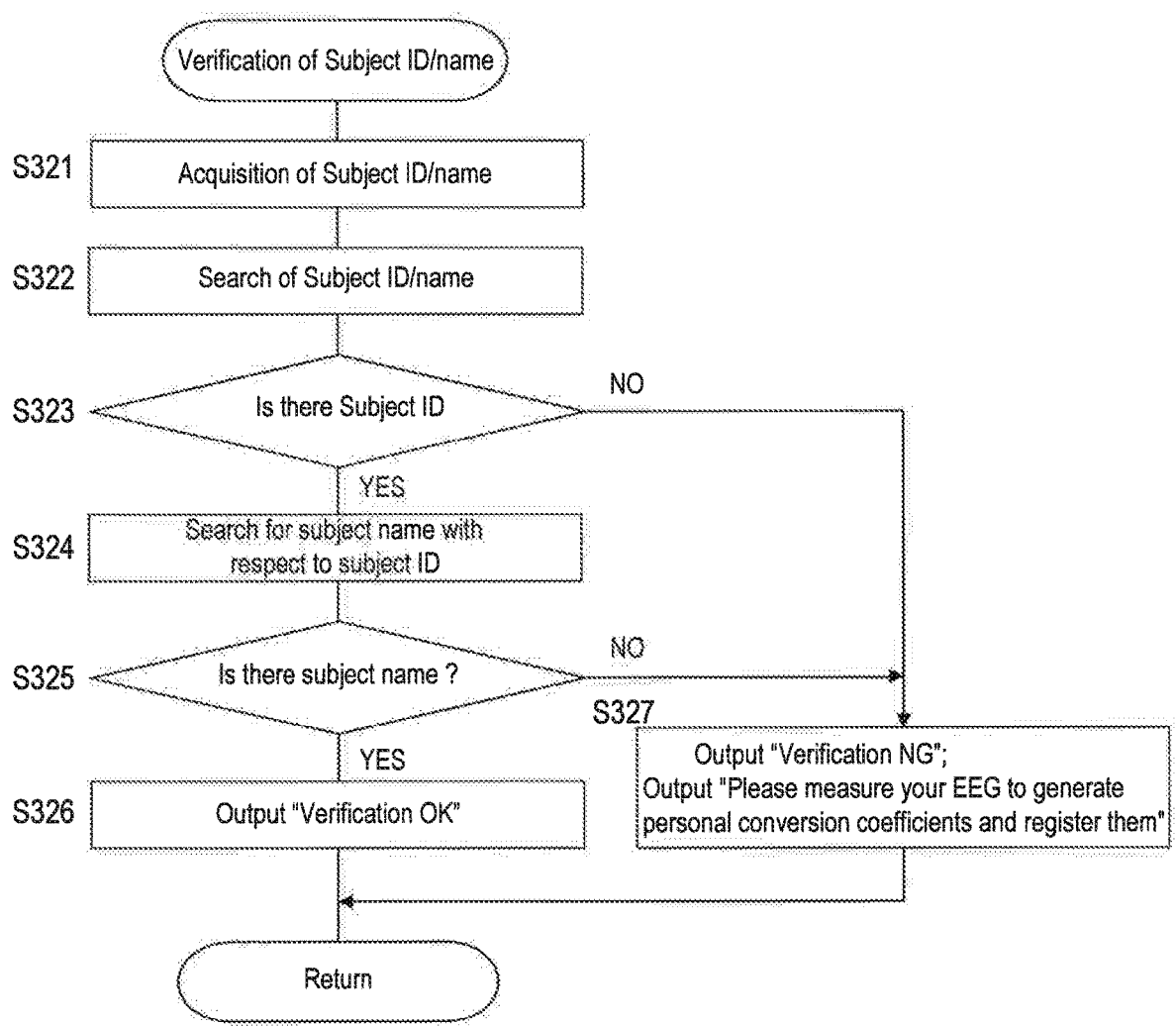
FIG. 14 is a subroutine flowchart of step S320 (subject ID/subject name collation) of the main flowchart of FIG. 13.

FIG. 14 is a flowchart of subroutine of step S320 (collation of subject ID/subject name) in the main flowchart of FIG. 13. This subroutine flowchart is processed by the electroencephalogram generation unit 250.

The electroencephalogram generation unit 250 acquires the subject ID and the subject name from the subject information input unit 220 (step S321).

The electroencephalogram generation unit 250 searches for subject IDs stored in the subject information storage units 270 and 353C (step Ss322).

If there is the same subject ID as the subject ID inputted from the subject information input unit 220 in any of the subject information storage units 270 and 353C (step S323: YES), the electroencephalogram generation unit 250 searches subject name stored in the subject information storage units 270 and 353C is searched (step S324).

If there is the same subject name as the subject name inputted from the subject information input unit 220 in any of the subject information storage units 270 and 353C (step S325: YES), a verification OK signal is outputted (Step S326).

When there is no subject ID identical to the subject ID entered from the subject information input unit 220 in any of the subject information storage units 270 and 353C (step S323: NO), or there is no subject name identical to the subject name entered from the subject information input unit 220 in any of the person information storage units 270 and 353C (step S325: NO), a signal of collation NG is outputted. The electroencephalogram generation unit 250 displays the message "Please measure your electroencephalogram in order to generate personal coefficients and register them" in the electroencephalogram display unit 260 (step S327).

Figure 15:
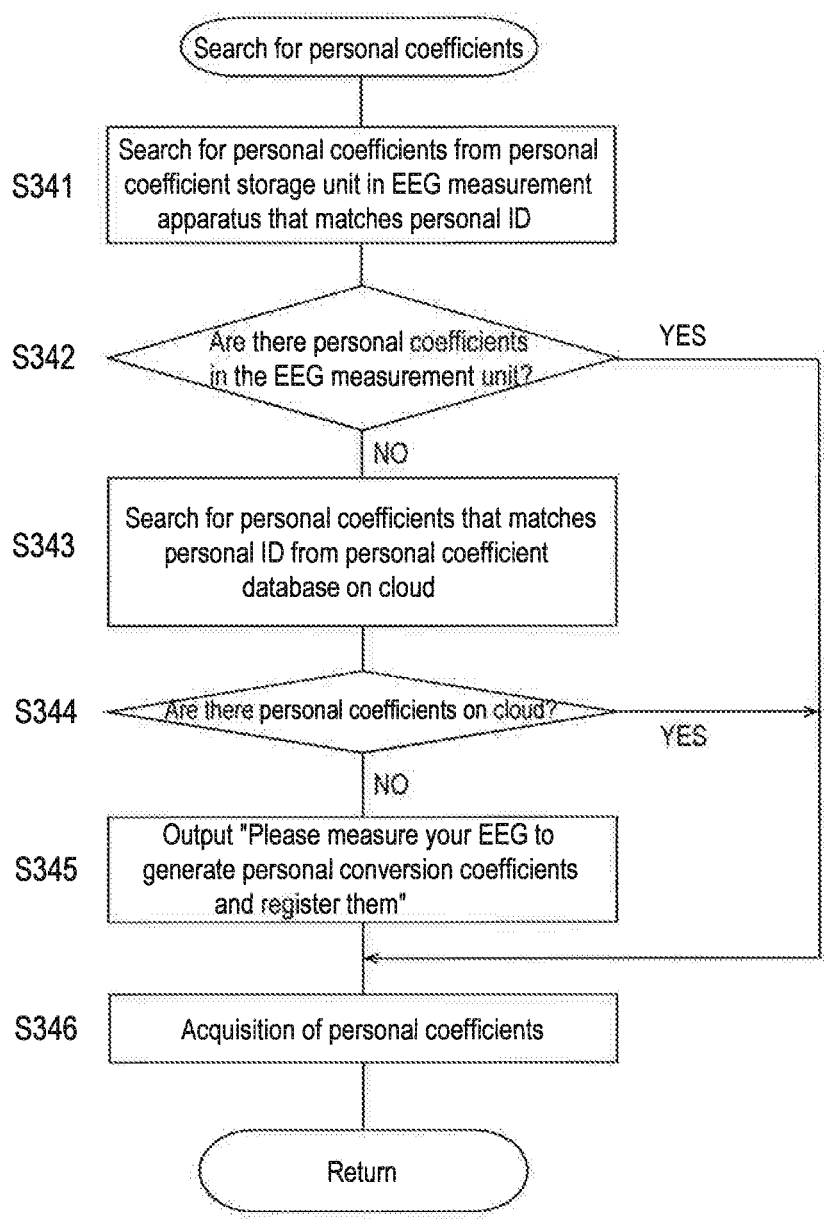
FIG. 15 is a subroutine flowchart of step S340 (personal coefficient search) of the main flowchart of FIG. 13.

FIG. 15 is a subroutine flowchart of step S340 (personal coefficient search) of the main flowchart of FIG. 13. This subroutine flowchart is processed by the electroencephalogram generation unit 250.

The electroencephalogram generation unit 250 searches for personal coefficients matching the subject ID from the personal coefficient storage unit 230 of the electroencephalogram measurement apparatus 200 (step S341).

If there is a personal coefficients of the subject in the electroencephalogram measurement apparatus 200 (step S342: YES), the electroencephalogram generation unit 250 acquires the personal coefficients from the personal coefficient storage unit 230 (step S346).

On the other hand, if there is no personal coefficients for the subject in the personal coefficient storage unit 230 of the electroencephalogram measurement apparatus 200 (step S342: NO), the electroencephalogram generation unit 250 searches the personal coefficient database 330C on the cloud 310 for the subject coefficients that match the subject (step S343).

If there is a personal coefficients of the subject on the cloud 310 (step S344: YES), the electroencephalogram generation unit 250 acquires the personal coefficient from the personal coefficient database 330C (step S346).

On the other hand, if there is no personal coefficient of the subject in the personal coefficient database 330C on the cloud 310 (step S344: NO), the electroencephalogram generation unit 250 instructs the electroencephalogram display unit 260 to "Please measure your electroencephalogram in order to generate personal coefficients and register them" (step S345).

Figure 16:
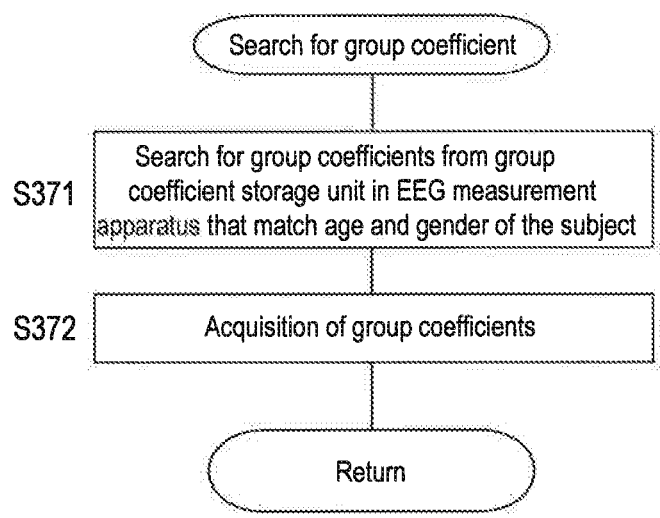
FIG. 16 is a subroutine flowchart of step S370 (group coefficient search) of the main flowchart of FIG. 13. FIG.

FIG. 16 is a subroutine flowchart of step S370 (collective coefficient search) of the main flowchart. This subroutine flowchart is processed by the electroencephalogram generation unit 250.

The electroencephalogram generation unit 250 searches for group coefficients that match the subject's age and subject gender from the group coefficient storage unit 240 of the electroencephalogram measurement apparatus 200 (step S371).

The electroencephalogram generation unit 250 acquires the group coefficient from the group coefficient storage unit 240 of the electroencephalogram measurement apparatus 200 (step S372).

Figure 17:
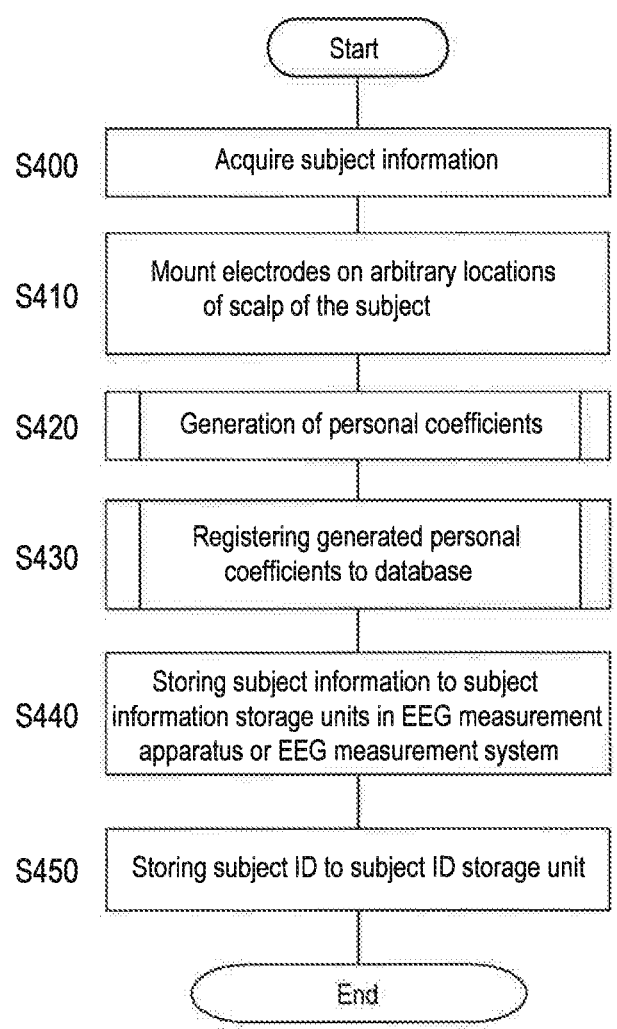
FIG. 17 is a main flowchart showing a process of generating personal coefficients of a subject and storing the generated personal coefficients in the personal coefficient database.

FIG. 17 is a main flowchart showing the process of generating personal coefficients of a subject and storing the generated personal coefficients in the personal coefficient database. This main flow chart is processed by the electroencephalogram generation unit 250.

The electroencephalogram generation unit 250 acquires information on the subject inputted from the subject information input unit 220. Information of the subject is the subject ID, name, age, gender. Among the information on the subject, the subject ID and subject name are used when storing the personal coefficients of the subject in the personal coefficient database (step S400).

The electroencephalogram generation unit 250 acquires electroencephalogram signals of arbitrary measurement locations from a plurality of electroencephalogram measurement electrodes 210 attached on the subject's scalp (step S410). The electroencephalogram measurement electrodes 210 can be attached to all the necessary locations on the scalp as shown in FIG. 4 for the subject who wish to acquire the electroencephalogram. Specifically, when the international 10-20 system is used as shown in FIG. 4, the locations are FP1, FP2, F7, F3, Fz, F4, F8, T3, C3, Cz, C4, T4, P3, Pz, P4, T5, O1, O3, Oz, O4, O2, and T6, 22 locations in total. In the case of using HEEG, electroencephalogram measurement electrodes 110 may have a number between 64 to 200 locations.

The electroencephalogram generation unit 250 substitutes values of electroencephalograms actually measured by the measurement electrodes 210 into equation 1 to calculate the personal coefficients of the subject (coefficients in B (b 11, b 12, . . . , b1n, b 21, B 22, . . . , B2n, . . . , bn1, bn2, . . . , bnn)) (step S420).

Next, the electroencephalogram generation unit 250 stores the generated personal coefficients in the personal coefficient storage unit 230 and the personal coefficient database 330C on the cloud 310 on a subject-by-subject basis and in time series (step S430).

The electroencephalogram generation unit 250 stores the subject information acquired in step S400 in the subject information storage unit 270 of the electroencephalogram measurement apparatus 200 and at the same time stores onto the subject information storage unit 353C on the cloud 310 (see FIG. 11).

In storing the information of the subject in the subject information storage unit 353C, the electroencephalogram generation unit 250 transmits information of the subject from the communication unit 280 via the connection line 320 to the personal coefficient control unit 354C. Next, the information of the subject received by the personal coefficient control unit 354C is stored in the subject information storage unit 353C (step S440).

The electroencephalogram generation unit 250 stores the subject ID in the subject information acquired in step S400 in the subject ID database 394C of the subject ID management unit 390C, In the case of storing the subject ID in the subject ID database 394C, the electroencephalogram generation unit 250 transmits the subject ID from the communication unit 280 via the connection line 320, and transmits the subject ID to the subject ID management unit 390C. The subject ID converting unit 392C receives e subject ID via the communication unit 396C. Next, the subject ID received by the subject ID converting unit 392C is stored in the subject ID database 394C (step S450).

Figure 18:
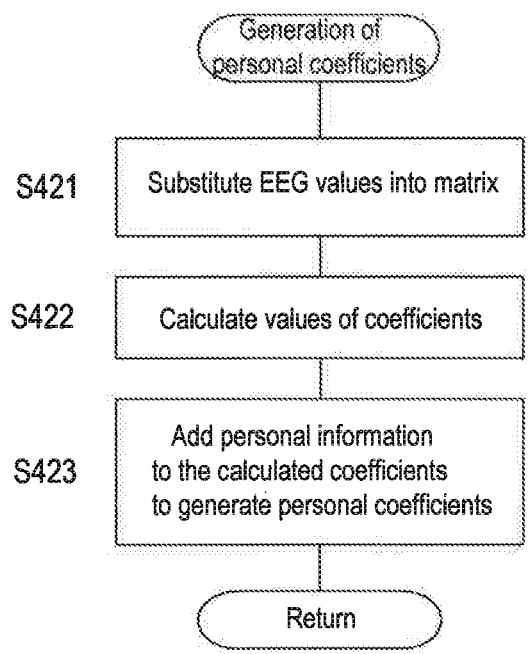
FIG. 18 is a subroutine flowchart showing processing of step S420 (generation of personal coefficients) of the main flowchart of FIG. 17.

FIG. 18 is a subroutine flowchart showing the processing of step S420 (generation of personal coefficients) in the main flowchart of FIG. 17.

The electroencephalogram generator 250 substitutes values of the electroencephalogram signals actually measured by the electroencephalogram measurement electrodes 210 attached to the subject into the measurement lead vector A (a1, a2, a3, . . . , an), and into the generation lead vector C (c1, c2, c3, . . . , Cn) in equation 1 (step S421).

The electroencephalogram generation unit 250 calculates the value of the coefficients in matrix B. Described in details, a simultaneous equation of A·B=C is prepared, and the simultaneous equations are solved to obtain coefficients in B (b11, b12, ..., b1n, b21, b22, ..., b2n, ..., bn1, bn2, ..., bnn) (step 422). Personal coefficients are calculated with respect to electroencephalogram itself, and the electroencephalogram components.

Finally, the electroencephalogram generation unit 250 adds information of the subject to the obtained coefficients to generate personal coefficients (step S423). For example, the information of the subject to be added is the subject ID. In this case, they are the unique ID "C123" and the subject ID "A123".

Figure 19:
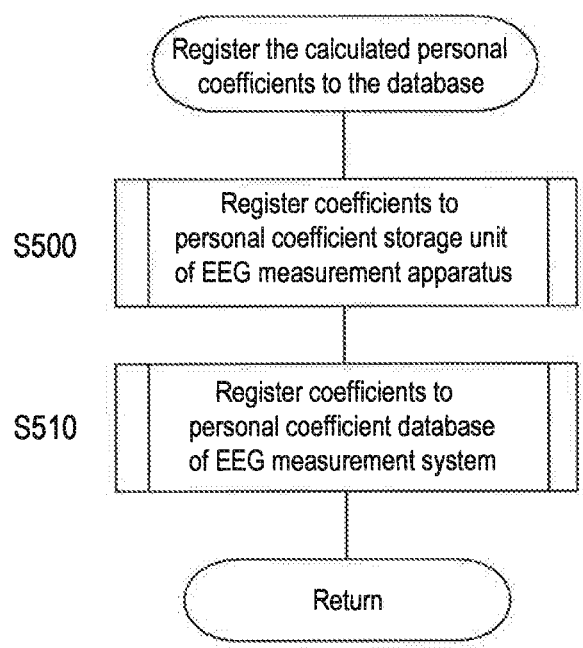
FIG. 19 is a subroutine flowchart showing the processing of step S430 (registering the generated personal coefficient in the database) of the main flowchart of FIG. 17.

FIG. 19 is a subroutine flowchart showing the process of step S430 (registering the generated personal coefficient in the database) of the main flowchart of FIG. 17. This flowchart is processed by the electroencephalogram generation unit 250 and the personal coefficient management unit 350C.

First, the electroencephalogram generation unit 250 registers the generated personal coefficients in the personal coefficient storage unit 230.

Next, the personal coefficient management unit 350C stores the personal coefficients sent from the electroencephalogram generation unit 250 in the personal coefficient database 330C. Detailed processing of these steps is shown in the subroutine flowchart of FIG. 20 and FIG. 21.

Figure 20:
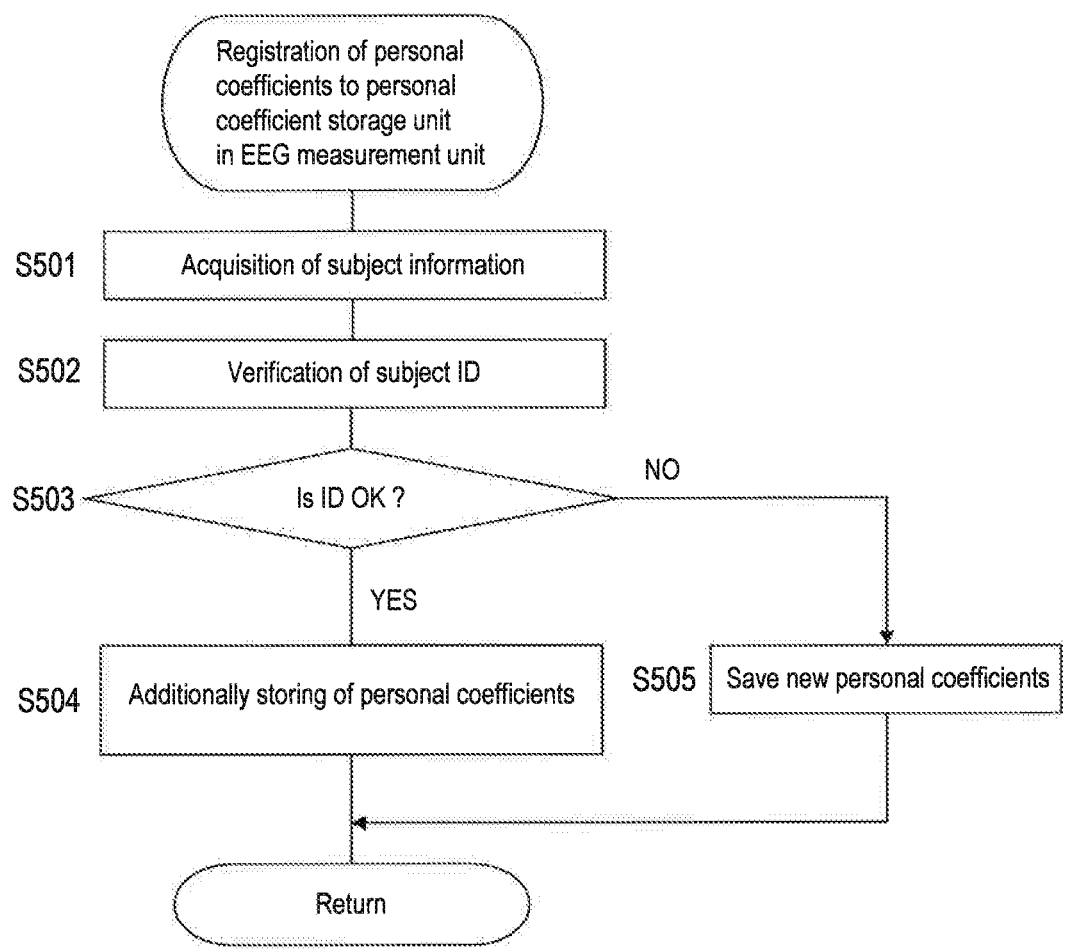
FIG. 20 is a subroutine flowchart showing processing of step S500 (register to the personal coefficient storage unit of the electroencephalogram measurement apparatus) of the subroutine flowchart of FIG. 19.

FIG. 20 is a subroutine flowchart showing processing of step S500 (storage in the personal coefficient storage unit of the electroencephalogram measurement apparatus) of the subroutine flowchart of FIG. 19. This flowchart is processed by the electroencephalogram generation unit 250.

First, the electroencephalogram generation unit 250 acquires information on the subject inputted from the subject information input unit 220 (step S501). Information on the subject may be the subject's ID, name, age, gender, etc.

The electroencephalogram generation unit 250 verifies the subject ID with the subject IDs stored in the subject information storage units 270 and 353C (step S502).

If there is a subject ID that matches the subject information storage units 270 and 353C, the verification is OK (step S503: YES) then electroencephalogram generation unit 250 additionally stores the coefficients to personal coefficient storage unit 230. In other words, when the same subject already has personal coefficients, newly generated personal coefficients are additionally stored in chronological order. By updating the personal coefficients in chronological order, it is always possible to select optimum coefficients of the subject, to ensure highly accurate electroencephalogram generation (step S504).

On the other hand, when there is no matching subject ID in the subject information storage units 270 and 353C and the verification is not successful (step S503: NO), the electroencephalogram generation unit 250 saves new personal coefficients in the personal coefficient storage unit 230 (step S505).

Figure 21:
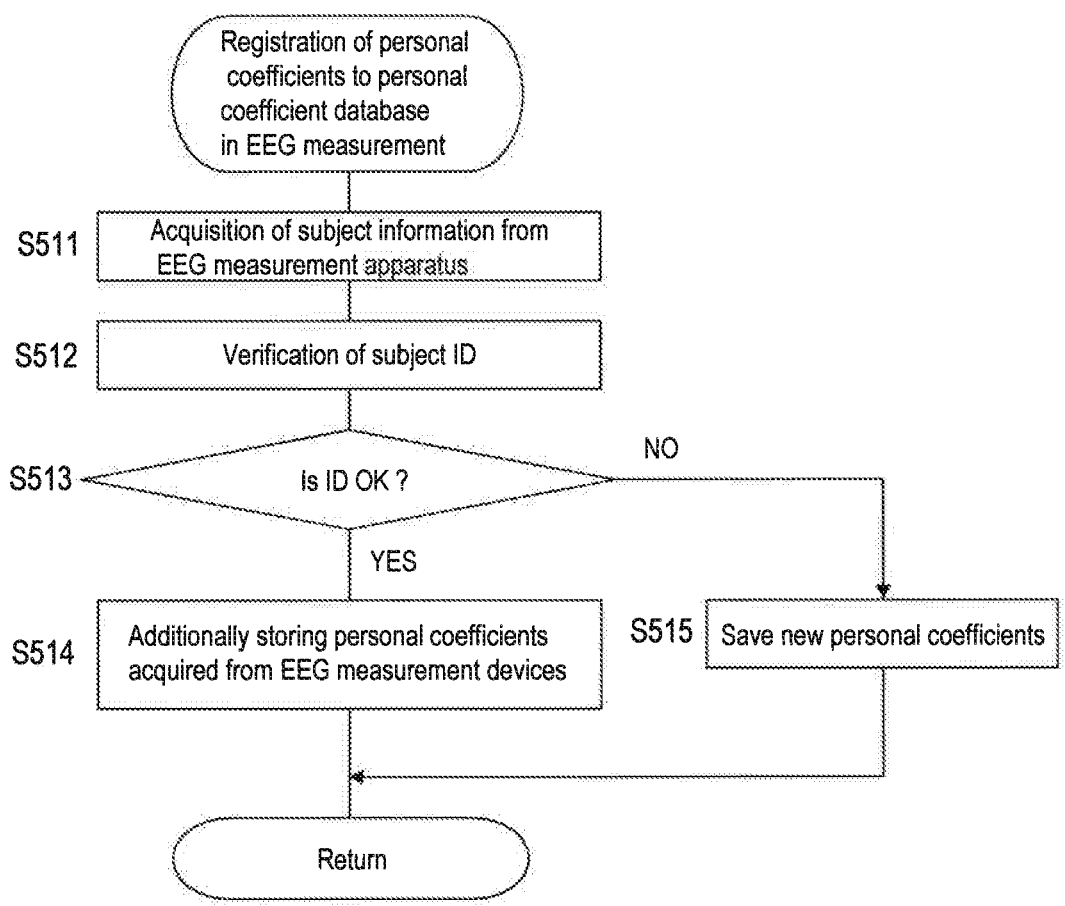
FIG. 21 is a subroutine flowchart showing processing of step S510 (register to the personal coefficient database of the electroencephalogram measurement system) of the subroutine flowchart of FIG. 19.

FIG. 21 is a subroutine flowchart showing the processing of step S510 (storage in the personal coefficient database of the electroencephalogram management system) of the subroutine flowchart of FIG. 19. This flowchart is processed by the personal coefficient control unit 354C.

First, the personal coefficient control unit 354C on the cloud 310 acquires information on the subject from the electroencephalogram measurement apparatus 200. The information of the subject may be the subject's ID, name, age, gender, etc. (step S511).

The personal coefficient control unit 354C verifies the subject ID with the subject ID stored in the subject information storage unit 353C (step S512).

If there is a subject ID that matches the subject information storage unit 353C, the verification is OK (step S513: YES). The personal coefficient control unit 354C stores the personal coefficient of the subject in the personal coefficient database 330C. In other words, when the same subject already has personal coefficients, newly generated personal coefficients are additionally stored in chronological order.

On the other hand, when there is no matching subject ID in the subject information storage unit 353C and there is no verification (NG in step S513), since there are no personal coefficients of the subject in the personal coefficient database 330C, the coefficient management unit 350C saves new personal coefficients in the personal coefficient database 330C (step S515).

As described above, with the electroencephalogram measurement system according to the present embodiment, the electroencephalograms at the locations where the electroencephalogram measurement electrodes 110 are not actually attached can be generated with high accuracy from the electroencephalograms at the locations where the electroencephalogram measurement electrode 110 are attached, by using personal coefficients or group coefficients.

Therefore, according to the electroencephalogram measurement system according to the present embodiment, high-resolution electroencephalograms can be measured with fewer electrodes, which can greatly contribute to practical application of BCI.

In the present embodiment, the personal coefficients are stored in chronological order for each subject, but when the storage capacity of the electroencephalogram measurement apparatus is small, instead of using time series of coefficients, the latest personal coefficients can be used, updated and stored each time. Further, in the present embodiment, the personal coefficients can be used even if they are stored two or three years ago, for example. However, in order to be able to generate electroencephalogram of a subject with high accuracy, it is desirable to generate an electroencephalogram by using personal coefficients acquired as close as possible. Therefore, when the expiration date of use (for example, one year from the acquisition) of the personal coefficient is set and when the expiration date has passed, urges acquisition of new personal coefficients in the same manner as when there is no personal coefficients, as shown in the processing flowchart in FIG. 17.

Note that the present invention is not limited to the above-described embodiments. The technical scope of the present invention encompasses other embodiments that can be modified by a person having ordinary knowledge in the field of the technology besides the above embodiment.

EXPLANATION OF SIGNS 100, 200, 200A, 200B electroencephalogram measurement apparatus
110, 210 electroencephalogram measurement electrodes
120, 220 subject information input unit
130, 230 personal coefficient storage unit
140, 240 group coefficient storage unit
150, 250 electroencephalogram generate unit
160 electroencephalogram output unit
260 electroencephalogram display unit
270, 353C subject information storage unit
280, 55C, 396C communication unit
310 cloud 320 connection line
330C personal coefficient database
350C personal coefficient management unit
354C personal coefficient control unit
390C subject ID management unit
392C subject ID conversion unit
394C subject ID database

What is claimed is:

1. An electroencephalogram measurement apparatus comprising:
a plurality of electrodes configured to be attached on a scalp of a subject for acquisition of electroencephalogram signals of said subject, and
an electroencephalogram generation processor for generating an electroencephalograms signals at locations of the scalp where said electrodes are attached and electroencephalograms signals at locations of the scalp where said electrodes are not attached, wherein said electroencephalogram measurement apparatus further comprises
a subject information input database that inputs information of the subject;
and a group coefficient storage database for storing group coefficients which are generated by statistically processing coefficients acquired from unspecified number of people of a population for generating electroencephalogram signals of said subject; and
a personal coefficient storage database for storing personal coefficients generated from electroencephalogram signals acquired from said subject for generation of electroencephalogram signals of said subject; and
when there is the personal coefficient that match information of said subject inputted from said subject information input database in said personal coefficient storage database, said electroencephalogram generation processor generates the electroencephalograms signals at the locations of the scalp of said subject on which said electrodes are not attached by using the electroencephalogram signals acquired from said plurality of electrodes and the personal coefficients of said subject, and when there is no personal coefficients that match the information of said subject inputted from the subject information input database in said personal coefficient storage database, said electroencephalogram generation processor generates the electroencephalograms signals at the locations of the scalp of said subject on which said electrodes are not attached by using the electroencephalogram signals acquired from said plurality of electrodes and said group coefficients.

2. An electroencephalogram measurement system, wherein a plurality of electroencephalogram measurement apparatus of claim 1 are connected to each other via connection lines; and
the personal coefficient database is provided on a cloud connected to said connection lines; and when there is the personal coefficient in said
electroencephalogram measurement apparatuses or said cloud that match information of said subject, the electroencephalogram generation unit in each of said
electroencephalogram measurement apparatuses generates electroencephalograms signals at the locations of the scalp where said electrodes are not attached, by using the electroencephalogram signals acquired from said plurality of electrodes and said personal coefficients of the subject, and when there is no personal coefficient that match the information of said subject, said electroencephalogram generation processor generates electroencephalograms signals at the locations of the scalp of said subject where said electrodes are not attached, by using the electroencephalogram signals acquired from said plurality of electrodes and group coefficients stored in the group coefficient storage database in said electroencephalogram measurement apparatuses.

3. The electroencephalogram measurement system of claim 2, further comprising:
a personal coefficient management database for managing said personal coefficients of said personal coefficient database, and
a subject ID management database for managing information of said subject on said cloud; wherein said personal coefficient management database stores personal coefficients in said personal coefficient database or extract personal coefficients from said personal coefficient database by using unique IDs associated with said subject's personal coefficients, said person ID management database has a lookup table between said unique ID and said subject ID attached to said subject, and when said electroencephalogram measurement apparatus searches on said cloud for said personal information of said subject, said unique ID of said subject is searched by using said lookup table in said subject ID management database, and said personal coefficient of said subject is obtained from said personal coefficient management database by using the unique ID.

4. An electroencephalogram measurement system of claim 3, wherein said subject ID management database has the lookup table indicating the relationship between said subject ID and the unique ID, and each of said electroencephalogram measurement apparatuses extracts said personal coefficients of said subject from said personal coefficient management database by using the unique ID.

5. The electroencephalogram measurement system of claim 2, wherein said electroencephalogram generation processor generates said electroencephalogram signals for a delta wave, theta wave, alpha wave, beta wave, or gamma wave.

6. The electroencephalogram measurement system of claim 5, wherein said personal coefficient, is provided for each of said delta wave, theta wave, alpha wave, beta wave, or gamma wave.

7. The electroencephalogram measuring system of claim 5, wherein said group coefficient, is provided for each of said delta wave, theta wave, alpha wave, beta wave, or gamma wave.

8. An electroencephalogram measurement method comprising, steps of: attaching a plurality of electrodes on a scalp of a subject and input information of said subject;
acquiring electroencephalogram signals of said subject from said plurality of electrodes; and generating electroencephalograms at locations of the scalp where said electrodes are attached and locations of the scalp where said electrodes are not attached, and when there are personal coefficients that match information of said subject, said step of generating electroencephalogram generates electroencephalograms at the locations of the scalp where said electrodes are not attached by using electroencephalogram signals acquired from said plurality of electrodes and said personal coefficients of said subject, and when there are no personal coefficients that match the information of said subject, said step of generating electroencephalogram generates electroencephalograms at the locations of the scalp where said electrodes are not attached by using electroencephalogram signals acquired from said plurality of electrodes and group coefficients.

9. The electroencephalogram measurement method of claim 8, wherein personal coefficients are provided that match information of said subject.

* * * * *